(12) United States Patent
Hoare

(10) Patent No.: US 9,782,398 B2
(45) Date of Patent: Oct. 10, 2017

(54) PHARMACEUTICAL COMPOSITIONS COMPRISING AN ANTIPSYCHOTIC DRUG AND A VMAT2 INHIBITOR AND USES THEREOF

(71) Applicant: NEUROCRINE BIOSCIENCES, INC., San Diego, CA (US)

(72) Inventor: Samuel Roger Jesse Hoare, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 29 days.

(21) Appl. No.: 15/116,786

(22) PCT Filed: Feb. 6, 2015

(86) PCT No.: PCT/US2015/014893
§ 371 (c)(1),
(2) Date: Aug. 4, 2016

(87) PCT Pub. No.: WO2015/120317
PCT Pub. Date: Aug. 13, 2015

(65) Prior Publication Data
US 2016/0339011 A1 Nov. 24, 2016

Related U.S. Application Data

(60) Provisional application No. 61/937,223, filed on Feb. 7, 2014.

(51) Int. Cl.
| | | |
|---|---|---|
| *A61K 31/519* | (2006.01) | |
| *A61K 31/5517* | (2006.01) | |
| *A61K 31/473* | (2006.01) | |
| *A61K 31/4745* | (2006.01) | |
| *A61K 31/551* | (2006.01) | |
| *A61K 45/06* | (2006.01) | |
| *A61K 31/5513* | (2006.01) | |

(52) U.S. Cl.
CPC ........ *A61K 31/473* (2013.01); *A61K 31/4745* (2013.01); *A61K 31/519* (2013.01); *A61K 31/551* (2013.01); *A61K 31/5513* (2013.01); *A61K 45/06* (2013.01)

(58) Field of Classification Search
CPC . A61K 31/145; A61K 31/519; A61K 31/5517
USPC ............................................. 514/220, 259.41
See application file for complete search history.

(56) References Cited

FOREIGN PATENT DOCUMENTS

| WO | 98/11897 A1 | 3/1998 |
|---|---|---|
| WO | WO-9811897 | * 3/1998 |
| WO | 00/24399 A1 | 5/2000 |
| WO | 2005/077946 A1 | 8/2005 |
| WO | 2007/017654 A1 | 2/2007 |
| WO | 2008/058261 A1 | 5/2008 |
| WO | 2010/026436 A2 | 3/2010 |
| WO | 2010/044981 A2 | 4/2010 |
| WO | 2011/019956 A2 | 2/2011 |

OTHER PUBLICATIONS

Hu, "New Fluorescent Substrate Enables Quantitative and High-throughput Examination of Vesicular Monoamine Transporter 2 (VMAT2)," ACS Chem Biol. Sep. 20, 2013: 8(9): 1947-1954.*
Healy et al., "Clozapine-reserpine combination for refractory psychosis," *Schizophrenia Research* 25:259-260, Jan. 1, 1997.
Kimiagar et al., "Rapid improvement of tardive dyskinesia with tetrabenazine, clonazepam and clozapine combined: a naturalistic long-term follow-up study," *J. Neurol.* 259(4): 660-664, Nov. 9, 2011.
Koch et al., "Successful Therapy of Tardive Dyskinesia in a 71-Year-Old Woman With a Combination of Tetrabenazine, Olanzapine and Tiapride," *IJCP* 57(2):147-149, Mar. 1, 2003.
Piccinni et al., "Effectiveness of a Clozapine-Aripiprazole Combination in Tourette Syndrome and Bipolar Spectrum Disorder," *J Neuropsychiatry Clin Neurosci* 25:1, Jan. 1, 2013.
Remington et al., "Tetrabenazine Augmentation in Treatment-Resistant Schizophrenia," *Journal of Clinical Psychopharmacology* 32(1):95-99, Feb. 1, 2012.
Solon, Earl N., "Risperidone-reserpine combination in refractory psychosis," *Schizophrenia Research* 22(3):265-266, Dec. 1, 1996.
Spina et al., "Effect of Fluoxetine on the plasma concentrations of clozapine and its major metabolites in patients with schizophrenia," *International Clinical Psychopharmacology* 13(3):141-145, May 1, 1998.
Tandon et al., "World Psychiatric Association Pharmacopsychiatry Section statement on comparative effectiveness of antipsychotics in the treatment of schizophrenia," *Schizophrenia Research* 100(1-3):20-38, Mar. 1, 2008.
Yasumoto et al., "Inhibitory effect of selective serotonin reuptake inhibitors on the vesicular monoamine transporter 2," *Neuroscience Letters* 454(3):229-232, May 1, 2009.
Zhang et al., "Synergistic Effects of Olanzapine and Other Antipsychotic Agents in Combination with Fluoxetine on Norepinephrine and Dopamine Release in Rate Prefrontal Cortex," *Neuropsychopharmacology* 23(3):250-262, Sep. 1, 2000.

* cited by examiner

*Primary Examiner* — Yong Chu
*Assistant Examiner* — Sonya Wright
(74) *Attorney, Agent, or Firm* — Seed IP Law Group LLP

(57) ABSTRACT

New methods of treating schizophrenia and schizoaffective disorder by administration of pharmaceutical compositions comprising an antipsychotic compound and a VMAT2 inhibitor to a subject in need thereof are provided.

12 Claims, 8 Drawing Sheets

PHARMACEUTICAL COMPOSITIONS COMPRISING AN ANTIPSYCHOTIC DRUG AND A VMAT2 INHIBITOR AND USES THEREOF

BACKGROUND

Technical Field

Provided herein are methods of treating schizophrenia, schizoaffective disorder, bipolar disease, major depressive disorder and other conditions commonly treated with antipsychotic medication by administering to a subject in need thereof a pharmaceutical composition comprising an antipsychotic compound and a VMAT2 inhibitor.

Description of the Related Art

Schizophrenia affects approximately 1% of the adult population and reduces life expectancy by an average of 20 to 25 years through the impact of the disorder on self-care and physical health, as well as through suicide. At the present time the etiological mechanisms underlying schizophrenia are poorly understood. Schizophrenia is diagnosed clinically, based on characteristic symptoms of psychosis, disorganization and so called 'negative' symptoms (representing a reduced range of emotional expression, reduced production of speech and a lack of volition/motivation); duration of illness; impaired functioning; and the exclusion of other disorders such as autism and bipolar disorder. For clinicians, identifying which psychotic patients have schizophrenia requires clinical acumen and familiarity with the DSM-IV or ICD-10 diagnostic manuals (see, e.g., Corvin, BMC Biol. 2011; 9: 77).

Antipsychotic drug therapy is a pillar in the treatment of schizophrenia. These antipsychotic drugs, also known as neuroleptics, generally cause a reduction of the 'positive' symptoms of schizophrenia, namely psychosis, thought disorders, and disorganized behavior. Antipsychotics generally have a lesser influence on cognition and on the 'negative' symptoms of the disease, which include lack of motivation and emotion, social withdrawal, lack of interest in everyday activities, and the reduced ability to plan or carry out activities.

First generation or "typical" antipsychotics have been used for over 50 years in the treatment of schizophrenia and other psychotic disorders. The first marketed antipsychotic was chlorpromazine; other typical antipsychotics include fluphenazine, haloperidol, loxapine, molindone, perphenazine, pimozide, sulpiride, thioridazine, and trifluoperazine. These typical antipsychotics all gain their primary efficacy through D2 dopamine receptor antagonism and have a propensity to cause movement disorders including parkinsonism (tremor, rigidity, bradykinesia and gait instability) as well as dystonia, dyskinesia (e.g., tardive dyskinesia), and akathisia.

Second generation or "atypical" antipsychotics were developed, and these drugs possess a lower risk of causing TD and related movement disorders with chronic administration. These drugs include aripiprazole, asenapine, clozapine, iloperidone, olanzapine, paliperidone, quetiapine, risperidone, and ziprasidone. These atypical antipsychotics all exert their primary efficacy through D2 dopamine receptor antagonism with additional effects on receptors for other neurotransmitters. These atypical antipsychotics are associated with metabolic side effects sufficient to affect life expectancy. These side effects include a propensity to induce weight gain, as well as related metabolic disturbances such as hypertriglyceridemia and hyperglycemia. Clozapine appears to be the most effective as treatment for severe mental illness, but it has additional serious medical side effects, including a significant incidence of agranulocytosis that requires frequent monitoring of patients' white blood counts as a requirement for using the drug.

In addition to treatment of schizophrenia and schizoaffective disorder, certain antipsychotic medications have been approved as treatments of bipolar disorder, major depressive disorder (MDD), and autism spectrum disorders. Off-label use is prevalent, particularly of atypicals, which are used for the treatment of various conditions including anxiety, attention-deficit hyperactivity disorder (ADHD), dementia, depression, insomnia, obsessive-compulsive disorder (OCD), post-traumatic stress disorder, substance abuse, and Tourette's syndrome.

Because the side effects associated with administration of antipsychotic medications can significantly impact a patient's health and well-being, alternatives to the current therapies are needed.

BRIEF SUMMARY

Briefly, this disclosure relates to the discovery that the combination of an antipsychotic and a VMAT2 inhibitor shows therapeutic synergy and improves the therapeutic index of the antipsychotic in the treatment of neuropsychiatric disorders, such as schizophrenia, schizoaffective disorder, bipolar disease, major depressive disorder, and other conditions commonly treated with antipsychotic medications. Provided herein are new methods of treating diseases in patients who currently receive antipsychotics, and to pharmaceutical compositions useful in the treatment of neuropsychiatric disorders such as schizophrenia. More specifically, the methods described herein involve the administration of an antipsychotic and a VMAT2 inhibitor in combination. The present disclosure provides the following embodiments.

In one embodiment, a method is provided for treating a neuropsychiatric disorder in a subject comprising administering to the subject (a) an antipsychotic drug and (b) a VMAT2 inhibitor, wherein the therapeutically effective amount of the antipsychotic drug administered to the subject is less than the therapeutically effective amount of the antipsychotic drug when administered in the absence of the VMAT2 inhibitor. In certain embodiments, the neuropsychiatric disorder is schizophrenia, schizoaffective disorder, bipolar disorder, major depressive disorder (MDD), or autism. In particular embodiments, the antipsychotic drug and the VMAT2 inhibitor are administered concurrently. In other certain embodiments, the antipsychotic drug and the VMAT2 inhibitor are formulated in the same pharmaceutical composition. In another specific embodiment, the antipsychotic drug is formulated in a first pharmaceutical composition and the VMAT2 inhibitor is formulated in a second pharmaceutical composition. In certain embodiments, the antipsychotic drug is a typical antipsychotic drug. In a more specific embodiment, the typical antipsychotic drug is fluphenazine, haloperidol, loxapine, molindone, perphenazine, pimozide, sulpiride, thioridazine, or trifluoperazine. In yet another embodiment, the antipsychotic drug is an atypical antipsychotic drug. In a specific embodiment, the atypical antipsychotic drug is aripiprazole, asenapine, clozapine, iloperidone, olanzapine, paliperidone, quetiapine, risperidone, or ziprasidone. In a particular embodiment, the therapeutically effective amount of the antipsychotic drug is 10 to 90% less than the therapeutically effective amount of the antipsychotic drug when administered in the absence of the VMAT2 inhibitor. In an embodiment, the therapeutically effective amount of the antipsychotic drug is at least 25% less than the therapeutically effective amount of the antipsychotic drug when administered in the absence of the VMAT2 inhibitor. In an embodiment, the therapeutically effective amount of the antipsychotic drug is at least 50% less than the therapeutically effective amount of the antipsychotic drug when administered in the absence of the VMAT2 inhibitor. In a particular embodiment, the VMAT2 inhibitor is tetrabenazine (3-isobutyl-9,10-dimethoxy-1,3,4,6,7,11b-hexahydro-2H-pyrido[2,1-a]isoquinolin-2-one). In another specific embodiment, the VMAT2 inhibitor is (2R,3R,11bR)-3-isobutyl-9,10-dimethoxy-1,3,4,6,7,11b-hexahydro-2H-pyrido[2,1-a]isoquinolin-2-ol (R,R,R DHTBZ), and precursors thereof. In yet another specific embodiment, the VMAT2 inhibitor is (S)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester. In another embodiment, the VMAT2 inhibitor is deuterated tetrabenazine, particularly 3-isobutyl-9,10-$d_6$-dimethoxy-1,3,4,6,7,11b-hexahydro-2H-pyrido[2,1-a]isoquinolin-2-one ($d_6$-TBZ). In another embodiment, the VMAT2 inhibitor is [(2R,3S,11bR)-9,10-dimethoxy-3-(2-methylpropyl)-1H,2H,3H,4H,6H,7H,11bH-pyrido[2,1-a]isoquinolin-2-yl]methanol or a precursor thereof.

In one embodiment, a pharmaceutical preparation is provided for use in treating a neuropsychiatric disorder, the preparation comprising an antipsychotic drug and a VMAT2 inhibitor, wherein the preparation comprises an amount of the antipsychotic drug that is a subtherapeutic amount if used in the absence of the VMAT2 inhibitor. In a particular embodiment, the neuropsychiatric disorder is schizophrenia, schizoaffective disorder, bipolar disorder, major depressive disorder (MDD), or autism. In a certain embodiment, the antipsychotic drug is a typical antipsychotic drug. In a certain particular embodiment, the typical antipsychotic drug is fluphenazine, haloperidol, loxapine, molindone, perphenazine, pimozide, sulpiride, thioridazine, or trifluoperazine. In another particular embodiment, the antipsychotic drug is an atypical antipsychotic drug. In a more specific embodiment, the atypical antipsychotic drug is aripiprazole, asenapine, clozapine, iloperidone, olanzapine, paliperidone, quetiapine, risperidone, or ziprasidone. In another embodiment, the antipsychotic drug is formulated in a first pharmaceutical composition and the VMAT2 inhibitor is formulated in a second pharmaceutical composition. In a particular embodiment, the therapeutically effective amount of the antipsychotic drug is 10 to 90% less than the therapeutically effective amount of the antipsychotic drug when administered in the absence of the VMAT2 inhibitor. In still another specific embodiment, the therapeutically effective amount of the antipsychotic drug is at least 25% less than the therapeutically effective amount of the antipsychotic drug when administered in the absence of the VMAT2 inhibitor. In still another specific embodiment, the therapeutically effective amount of the antipsychotic drug is at least 50% less than the therapeutically effective amount of the antipsychotic drug when administered in the absence of the VMAT2 inhibitor. In one particular embodiment, the VMAT2 inhibitor is tetrabenazine (3-isobutyl-9,10-dimethoxy-1,3,4,6,7,11b-hexahydro-2H-pyrido[2,1-a]isoquinolin-2-one). In yet another particular embodiment, the VMAT2 inhibitor is (2R,3R,11bR)-3-isobutyl-9,10-dimethoxy-1,3,4,6,7,11b-hexahydro-2H-pyrido[2,1-a]isoquinolin-2-ol (R,R,R DHTBZ), or a precursor thereof. In still another certain embodiment, the VMAT2 inhibitor is (S)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester. In another embodiment, the VMAT2 inhibitor is deuterated tetrabenazine, particularly 3-isobutyl-9,10-$d_6$-dimethoxy-1,3,4,6,7,11b-hexahydro-2H-pyrido[2,1-a]isoquinolin-2-one ($d_6$-TBZ). In another embodiment, the VMAT2 inhibitor is [(2R,3S,11bR)-9,10-dimethoxy-3-(2-methylpropyl)-1H,2H,3H,4H,6H,7H,11bH-pyrido[2,1-a]isoquinolin-2-yl]methanol or a precursor thereof.

Also provided herein in another embodiment, is a method for enhancing efficacy of an antipsychotic drug comprising administering to a subject a combination of (a) the antipsychotic drug, and (b) a VMAT2 inhibitor. In one embodiment, enhancing efficacy of the antipsychotic drug comprises decreasing the amount of the antipsychotic drug that is therapeutically effective. In a particular embodiment, the therapeutically effective amount of the antipsychotic drug is 10 to 90% less than the therapeutically effective amount of the antipsychotic drug when administered in the absence of the VMAT2 inhibitor. In a specific embodiment, the amount of the antipsychotic drug that is therapeutically effective is at least 25% less than the amount of the antipsychotic drug that is therapeutically effective when the antipsychotic drug is administered in the absence of the VMAT2 inhibitor. In another specific embodiment, the amount of the antipsychotic drug that is therapeutically effective is at least 50% less than the amount of the antipsychotic drug that is therapeutically effective when the antipsychotic drug is administered in the absence of the VMAT2 inhibitor. In one embodiment, the antipsychotic drug is a typical antipsychotic drug. In a specific embodiment, the typical antipsychotic drug is fluphenazine, haloperidol, loxapine, molindone, perphenazine, pimozide, sulpiride, thioridazine, or trifluoperazine. In another embodiment, the antipsychotic drug is an atypical antipsychotic drug. In a more specific embodiment, the atypical antipsychotic drug is aripiprazole, asenapine, clozapine, iloperidone, olanzapine, paliperidone, quetiapine, risperidone, or ziprasidone. In another specific embodiment, the VMAT2 inhibitor is tetrabenazine (3-isobutyl-9,10-dimethoxy-1,3,4,6,7,11b-hexahydro-2H-pyrido[2,1-a]isoquinolin-2-one). In still another specific embodiment, the VMAT2 inhibitor is (2R,3R,11bR)-3-isobutyl-9,10-dimethoxy-1,3,4,6,7,11b-hexahydro-2H-pyrido[2,1-a]isoquinolin-2-ol(R,R,R DHTBZ), or a precursor thereof. In another particular embodiment, the VMAT2 inhibitor is (S)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester. In another embodiment, the VMAT2 inhibitor is deuterated tetrabenazine, particularly 3-isobutyl-9,10-$d_6$-dimethoxy-1,3,4,6,7,11b-hexahydro-2H-pyrido[2,1-a]isoquinolin-2-one ($d_6$-TBZ). In another embodiment, the VMAT2 inhibitor is [(2R,3S,11bR)-9,10-dimethoxy-3-(2-methylpropyl)-1H,2H,3H,4H,6H,7H,11bH-pyrido[2,1-a]isoquinolin-2-yl]methanol or a precursor thereof.

In another embodiment, a pharmaceutical preparation is provided that comprises an antipsychotic drug and a VMAT2 inhibitor, wherein the preparation is effective for treating a neuropsychiatric disorder, and wherein the amount of the antipsychotic drug is subtherapeutic compared with the therapeutic amount of the antipsychotic drug when used alone for treating the neuropsychiatric disorder in the absence of the VMAT2 inhibitor. In another embodiment, a pharmaceutical preparation is provided that comprises synergistically effective amounts of an antipsychotic drug and a VMAT2 inhibitor. In particular embodiments of the preparations, the antipsychotic drug is a typical antipsychotic drug. In specific embodiments, the typical antipsychotic drug is fluphenazine, haloperidol, loxapine, molindone, perphenazine, pimozide, sulpiride, thioridazine, or trifluoperazine. In other particular embodiments, the antipsychotic drug is an atypical antipsychotic drug. In more specific embodiments, the atypical antipsychotic drug is aripiprazole, asenapine, clozapine, iloperidone, olanzapine, paliperidone, quetiapine, risperidone, or ziprasidone. In still more specific embodiments, the VMAT2 inhibitor is tetrabenazine (3-isobutyl-9,10-dimethoxy-1,3,4,6,7,11b-hexahydro-2H-pyrido[2,1-a]isoquinolin-2-one). In other particular embodiments, the VMAT2 inhibitor is (2R,3R,11bR)-3-isobutyl-9, 10-dimethoxy-1,3,4,6,7,11b-hexahydro-2H-pyrido[2,1-a] isoquinolin-2-ol (R,R,R DHTBZ), or a precursor thereof. In still other particular embodiments, the VMAT2 inhibitor is (S)-2-Amino-3-methyl-butyric acid (2R,3R,11bR)-3-isobutyl-9,10-dimethoxy-1,3,4,6,7,11b-hexahydro-2H-pyrido[2, 1-a]isoquinolin-2-yl ester. In another embodiment, the VMAT2 inhibitor is deuterated tetrabenazine, particularly 3-isobutyl-9,10-$d_6$-dimethoxy-1,3,4,6,7,11b-hexahydro-2H-pyrido[2,1-a]isoquinolin-2-one ($d_6$-TBZ). In another embodiment, the VMAT2 inhibitor is [(2R,3S,11bR)-9,10-dimethoxy-3-(2-methylpropyl)-1H,2H,3H,4H,6H,7H, 11bH-pyrido[2,1-a]isoquinolin-2-yl]methanol or a precursor thereof. In other certain embodiments of the preparations, the antipsychotic drug and the VMAT2 inhibitor are formulated in the same pharmaceutical composition with at least one pharmaceutically acceptable excipient. In still other particular embodiments, the antipsychotic drug is formulated in a first pharmaceutical composition with at least one pharmaceutically acceptable excipient and the VMAT2 inhibitor is formulated in a second pharmaceutical composition with at least one pharmaceutically acceptable excipient. In certain embodiments, the neuropsychiatric disorder is schizophrenia, schizoaffective disorder, bipolar disorder, major depressive disorder (MDD), or autism.

These and other aspects of the invention will be apparent upon reference to the following detailed description. To this end, various references are set forth herein which describe in more detail certain background information, procedures, compounds and/or compositions, and are each hereby incorporated by reference in their entirety.

Terms not specifically defined herein should be given the meanings that would be given to them by one of skill in the art in light of the disclosure and the context. As used in the specification, however, unless specified to the contrary, the terms have the meaning indicated.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

DETAILED DESCRIPTION

Figure 1:
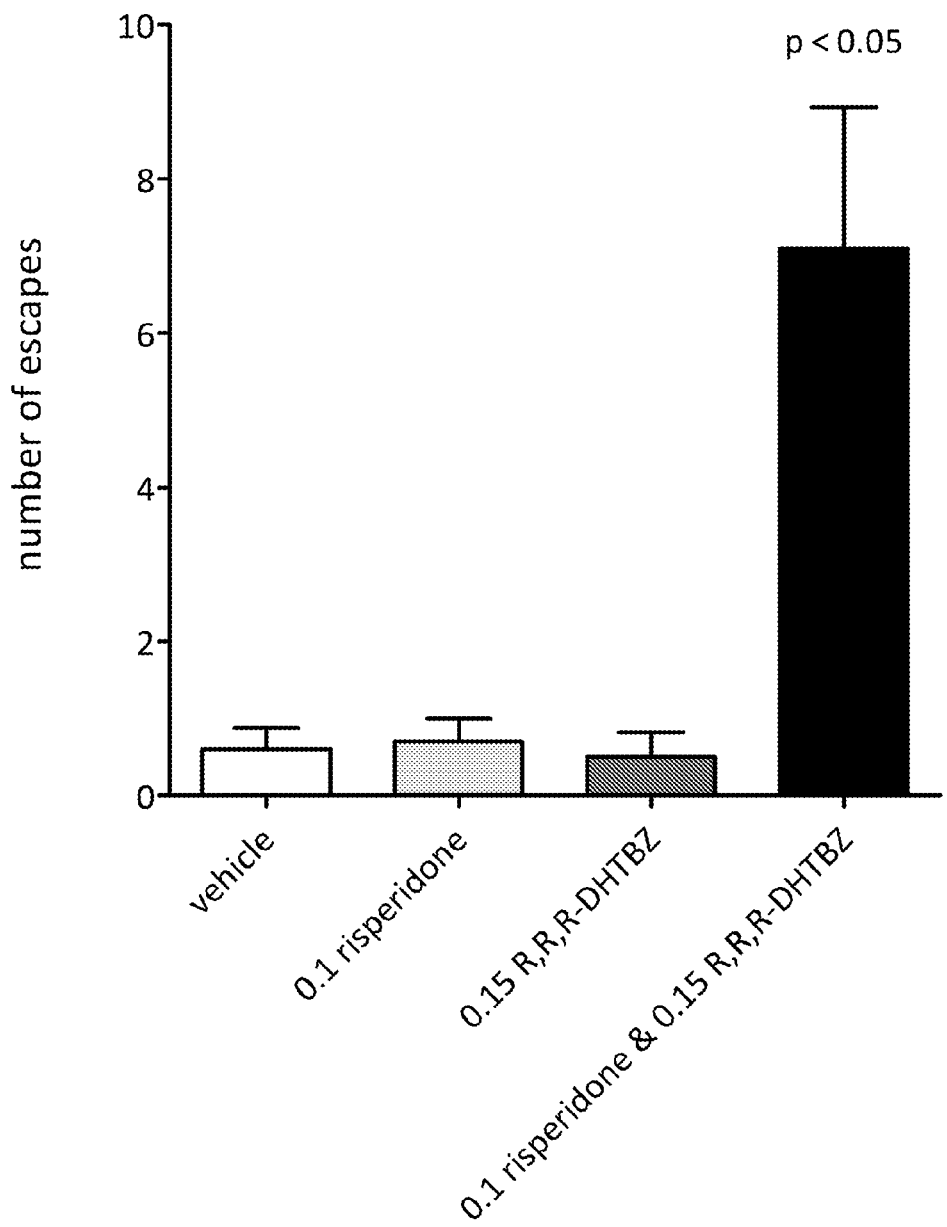
FIG. 1 shows the number of escapes in the Conditioned Avoidance Response (CAR) model as an indicator for antipsychotic activity. Vehicle, risperidone (0.1 mg/kg) singly, R,R,R DHTBZ singly (0.15 mg/kg), and a combination of risperidone 0.1 mg/kg) and R,R,R DHTBZ (0.15 mg/kg) were administered and the number of escapes measured.

A major drawback in treating schizophrenia and other conditions commonly treated with an antipsychotic (also called a neuroleptic) is the incidence of tardive dyskinesia (TD) that results from the administration of the antipsychotic therapy. Typical antipsychotic drugs (also called first generation antipsychotics) have a high incidence of extrapyramidal side effects, including tardive dyskinesia (TD). Second generation antipsychotic drugs (also called atypical antipsychotics) possess a lessened likelihood of causing TD but have other adverse effects such as weight gain and metabolic disturbances. Recent studies comparing the effectiveness of typical versus atypical antipsychotics show little difference in effectively treating psychosis even though the use of the second generation atypical antipsychotics greatly exceeds the current use of typical antipsychotics.

As disclosed herein, unexpectedly when a VMAT2 inhibitor is administered with an antipsychotic drug, the amount of antipsychotic administered may be reduced from the amount of the antipsychotic that is commonly administered to a subject due to a synergistic combination of the antipsychotic and the VMAT2 inhibitor. Administration of this combination results in more potent antipsychotic activity than observed when the antipsychotic drug is administered alone at the same dose. This reduction in dose can reduce the risk of occurrence of tardive dyskinesia associated with the antipsychotic drug, especially in the case of typical antipsychotic administration. Reducing the administered dose of an atypical antipsychotic agent by combining the atypical agent with a VMAT2 inhibitor may lessen or reduce the likelihood of occurrence, lessen or reduce time to onset of, and/or lessen or reduce the severity of the metabolic side effects (e.g., weight gain) often seen with these agents. In patients who have developed TD, the reduction in antipsychotic drug dose along with the presence of a potent VMAT2 inhibitor may thus be useful for treating TD while maintaining antipsychotic efficacy that is commensurate with antipsychotic efficacy observed when a higher dose of the antipsychotic alone is administered.

The methods, uses, and compositions described herein may have utility over a wide range of therapeutic applications, and may be used to treat a variety of neuropsychiatric conditions in a subject (i.e., patient, individual). For example, such conditions include neuropsychiatric conditions (e.g., schizophrenia, schizoaffective disorder, bipolar disease, major depressive disorder (MDD), manic depressive disorder, depression with psychotic features, delusional disorder and other psychotic conditions, the symptoms of hallucinations and delusions), and tardive dyskinesia. In a particular embodiment, methods are provided herein for treating a neuropsychiatric condition (for example, schizophrenia or schizoaffective disorder). Also provided are pharmaceutical compositions useful in the treatment of the aforementioned neuropsychiatric conditions, including schizophrenia or schizoaffective disorder. In other certain embodiments, the pharmaceutical compositions are useful in the treatment of a neuropsychiatric condition and tardive dyskinesia.

Antipsychotic Drugs and VMAT2 Inhibitors

The first marketed antipsychotic was chlorpromazine in 1952. This typical antipsychotic was followed by use of other typicals including fluphenazine, haloperidol, loxapine, molindone, perphenazine, pimozide, sulpiride, thioridazine, and trifluoperazine, or example. These typical antipsychotics all gain their primary efficacy through D2 dopamine receptor antagonism and have a propensity to cause movement disorders including parkinsonism (tremor, rigidity, bradykinesia and gait instability) as well as dystonia, dyskinesia, and akathisia.

In large cohort studies, tardive dyskinesia (TD) has been shown to affect at least one in five, and perhaps as many as one in three, patients treated chronically with first-generation antipsychotics. New onset (incidence) of TD is approximately 3% to 5% per year of treatment, and these rates are increased as much as five-fold in elderly patients (see, e.g., Lencz et al., *Dialogues Clin Neurosci.* 2009 December; 11(4): 405).

Tardive dyskinesia is a chronic disorder of the nervous system, characterized by involuntary movements most often involving the mouth, tongue, facial muscles, and to a lesser extent, the trunk and extremities. Most cases of TD are caused by long-term use of antipsychotic drugs. The condition can persist for months, years, or even permanently. In addition to physical discomfort and social stigma, presence of TD has been associated with reduced quality of life, increased psychopathology, and increased mortality rates. The etiology of TD is unknown, but antipsychotic drugs are hypothesized to cause TD through their dopamine antagonism.

Second generation or atypical antipsychotics were developed, and these drugs are believed to possess a lower risk of causing TD and related movement disorders when chronically administered. The incidence of TD with these drugs is as much as 80% lower than with typical neuroleptics. However, atypical antipsychotics cause side effects that include weight gain and related metabolic disturbances such as hypertriglyceridemia and hyperglycemia. Examples of atypical antipsychotic drugs include aripiprazole, asenapine, clozapine, iloperidone, olanzapine, paliperidone, quetiapine, risperidone, and ziprasidone. These atypical antipsychotics all exert their primary efficacy through D2 dopamine receptor antagonism with additional effects on receptors for other neurotransmitters.

Table 1 lists examples of typical antipsychotics and the range of recommended starting, target, and maximum daily doses for a reference case of a moderately symptomatic adult man with schizophrenia. Table 2 lists examples of atypical antipsychotics and the range of recommended starting, target, and maximum daily doses for a reference case of a moderately symptomatic adult man with schizophrenia (see, e.g., Gardner et al., *Am. J. Psychiatry* 2010: 167:686-693).

TABLE 1

Recommended Oral Dosing of Typical Antipsychotics (mg)

| Typical | Starting | Target | Maximum |
|---|---|---|---|
| fluphenazine | 3 | 5-15 | 20 |
| haloperidol | 3 | 5-10 | 20 |
| loxapine | 17.5 | 20-100 | 200 |
| molindone | 22.5 | 50-188 | 225 |
| perphenazine | 8 | 12-24 | 42 |
| pimozide | 2 | 4-6 | 10 |
| sulpiride | 100 | 300-600 | 1000 |
| thioridazine | 88 | 200-500 | 800 |
| trifluoperazine | 5 | 10-20 | 35 |

TABLE 2

Recommended Oral Dosing of Atypical Antipsychotics (mg)

| Atypical | Starting | Target | Maximum |
|---|---|---|---|
| Aripiprazole | 10 | 15-30 | 30 |
| Asenapine* | 10 | 10-20 | 20 |
| Clozapine | 25 | 200-500 | 800 |
| Iloperidone* | 2 | 12-24 | 24 |
| Olanzapine | 5 | 10-20 | 30 |

TABLE 2-continued

Recommended Oral Dosing of Atypical Antipsychotics (mg)

| Atypical | Starting | Target | Maximum |
|---|---|---|---|
| Paliperidone | 3 | 6-9 | 12 |
| Quetiapine | 100 | 400-800 | 1000 |
| Risperidone | 2 | 4-6 | 8.5 |
| Ziprasidone | 40 | 120-160 | 200 |

*Dosing as given in prescription package insert

For use in the methods and compositions described herein, the antipsychotic drug (or a physiologically acceptable salt thereof) may be a typical antipsychotic drug (i.e., first generation antipsychotic drug). The typical antipsychotic drug may be any one of fluphenazine, haloperidol, loxapine, molindone, perphenazine, pimozide, sulpiride, thioridazine, or trifluoperazine. In other embodiments, the antipsychotic drug (or a physiologically acceptable salt thereof) may be an atypical antipsychotic drug (i.e., second generation antipsychotic drug). The atypical antipsychotic drug may be any one of aripiprazole, asenapine, clozapine, iloperidone, olanzapine, paliperidone, quetiapine, risperidone, or ziprasidone.

The only option for preventing TD is to avoid use of antipsychotic drugs. When use of antipsychotic medication is necessary, as in the treatment of schizophrenia, use of the smallest possible dose of an antipsychotic for the shortest period of time possible is a desirable option. However, neither option is presently available for many schizophrenia patients who develop TD and must continue to receive antipsychotic therapy. Treatments for these TD patients involve changing or limiting the current antipsychotic therapy. For example, a first generation drug may be replaced with a second generation drug that has a lower risk of causing TD. Switching to a lower dose of the agent causing TD may also be helpful in alleviating symptoms. Changing drugs or lowering the dose of a first generation antipsychotic must be made, however, without exacerbating the underlying schizophrenia of the subject.

As described herein, administering an antipsychotic drug in combination with a VMAT2 inhibitor has a synergistic effect such that less of the antipsychotic drug needs to be administered to observe the same or similar efficacy than when the drug is administered alone. VMAT2 inhibitors (and physiologically acceptable salts thereof) may reduce the supply of monoamines in the central nervous system by inhibiting the vesicular monoamine transporter isoform 2 (VMAT2). Examples of VMAT2 inhibitors and monoamine depletors that may be used in the methods described herein include, for example, tetrabenazine (3-isobutyl-9,10-dimethoxy-1,3,4,6,7,11b-hexahydro-2H-pyrido[2,1-a]isoquinolin-2-one, TBZ). TBZ is approved for the treatment of chorea associated with Huntington's disease. Use of tetrabenazine for the treatment of TD and a variety of hyperkinetic movement disorders has also been described. Tetrabenazine is readily metabolized upon administration to dihydrotetrabenazine (3-isobutyl-9,10-dimethoxy-1,3,4,6,7,11b-hexahydro-2H-pyrido[2,1-a]isoquinolin-2-ol, DHTBZ), with the R,R,R stereoisomer of DHTBZ believed to be the most active metabolite. In certain embodiments, the methods described herein for treating a neuropsychiatric disorder comprise administering an antipsychotic drug and (2R,3R,11bR)-3-isobutyl-9,10-dimethoxy-1,3,4,6,7,11b-hexahydro-2H-pyrido[2,1-a]isoquinolin-2-ol (also called R,R,R-DHTBZ herein) or a precursor thereof. Other VMAT2 inhibitors that may be used in the methods and compositions described herein include TBZ analogs and metabolites, reserpine, lobeline and analogs, and compounds described in U.S. Pat. Nos. 8,039,627; 8,357,697; and 8,524,733. In one embodiment, the VMAT2 inhibitor is (S)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester (see U.S. Pat. No. 8,039,627). In another embodiment, the VMAT2 inhibitor is (2R,3R,11bR)-3-isobutyl-9,10-dimethoxy-1,3,4,6,7,11b-hexahydro-2H-pyrido[2,1-a]isoquinolin-2-ol (R,R,R DHTBZ). In still another embodiment, the VMATs inhibitor is [(2R,3S,11bR)-9,10-Dimethoxy-3-(2-methylpropyl)-1H,2H,3H,4H,6H,7H,11bH-pyrido[2,1-a]isoquinolin-2-yl]methanol (also called Compound 5-1 herein), or a precursor thereof (e.g., a prodrug of Compound 5-1). In yet another embodiment, the VMAT2 inhibitor is tetrabenazine or deuterated tetrabenazine. Deuterated tetrabenazine includes 3-isobutyl-9,10-$d_6$-dimethoxy-1,3,4,6,7,11b-hexahydro-2H-pyrido[2,1-a]isoquinolin-2-one ($d_6$-TBZ). As described herein, any one of the VMAT2 inhibitors may be combined with a pharmaceutically acceptable excipient, carrier, and/or diluent to form a pharmaceutical composition.

Characterizing the activity of a VMAT2 inhibitor can be readily determined using in vitro methods and animal models described in the art and herein (see, e.g., Teng, et al., *J. Neurochem.* 71, 258-65, 1998; Near, (1986), Near, (1986), *Mol. Pharmacol.* 30: 252-57). The capability of an antipsychotic drug to have a desired therapeutic effect may be determined using in vivo animal models, such as those described herein, which models are familiar to persons skilled in the art. The conditioned avoidance response (CAR) test has been shown to be an effective and reliable preclinical model for assessing the antipsychotic activity of compounds. Numerous studies have shown that typical and atypical antipsychotic drugs selectively suppress CAR, thus making it an ideal assay to screen for and to characterize antipsychotic compounds (see, e.g., Wadenberg et al., *Biobehav. Rev.* 1999, 23:851-62).

Persons skilled in the art readily appreciate that such assays and techniques are performed using appropriate negative controls (e.g., vehicle only, diluent only, etc.) and appropriate positive controls. Conditions for a particular in vitro assay include temperature, buffers (including salts, cations, media), and other components, which maintain the integrity of the test agent and reagents used in the assay, and which are familiar to a person skilled in the art and/or which can be readily determined. Determining the effectiveness of an antipsychotic drug in an animal model is typically performed using one or more statistical analyses with which a skilled person will be familiar. By way of example, statistical analyses such as two-way analysis of variance (ANOVA), Fisher's exact test, and/or Bonferroni Test, may be used for determining the statistical significance of differences between animal groups.

Compounds described herein include all polymorphs, prodrugs, isomers (including optical, geometric and tautomeric), salts, solvates and isotopes thereof. With regard to stereoisomers, the antipsychotics and VMAT2 inhibitors may have chiral centers and may occur as racemates, racemic mixtures and as individual enantiomers or diastereomers. All such isomeric forms are included, including mixtures thereof. Unless specifically indicated, throughout the specification and the appended claims, a given chemical formula or name shall encompass tautomers and all stereo, optical and geometrical isomers (e.g., enantiomers, diastereomers, E/Z isomers, etc.) and racemates thereof as well as mixtures in different proportions of the separate enantiomers, mixtures of diastereomers, or mixtures of any of the foregoing forms when such isomers and enantiomers exist, as well as salts thereof, including pharmaceutically acceptable salts thereof and solvates thereof such as for instance hydrates including solvates of the free compounds or solvates of a salt of the compound.

As used herein, pharmaceutically (or physiologically) acceptable salts refer to derivatives of the described compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (see also, e.g., Pharmaceutical Salts, Birge, S. M. et al., *J. Pharm. Sci.*, (1977), 66, 1-19).

In addition, prodrugs are also included with respect to the compounds described herein. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds as described herein wherein hydroxy, amine, or acid groups are bonded to any group that, when administered to a subject, cleaves to form the hydroxy, amine or acid groups. Thus, representative examples of prodrugs include (but are not limited to) acetate, formate and benzoate derivatives of alcohol and amine functional groups of a compound. Further, in the case of a carboxylic acid (—COOH), esters may be employed, such as methyl esters, ethyl esters, and the like.

The compounds described herein may exist in a continuum of solid states ranging from fully amorphous to fully crystalline. Furthermore, some of the crystalline forms of the compounds may exist as polymorphs. In addition, some compounds may also form solvates with water or other organic solvents. The term solvate is used herein to describe a molecular complex comprising a compound and one or more pharmaceutically acceptable solvent molecules.

The compounds described herein in certain embodiments are pharmaceutically acceptable isotopically labeled compounds wherein one or more atoms are replaced by atoms having the same atomic number but a different atomic mass. Examples include $^2H$ (deuterium) and $^3H$ (tritium) for hydrogen, $^{11}C$, $^{13}C$ and $^{14}C$ for carbon, $^{36}Cl$ for chlorine, $^{18}F$ for fluorine, $^{123}I$ and $^{125}I$ for iodine, $^{13}N$ and $^{15}N$ for nitrogen, and $^{35}S$ for sulfur. Examples also include the substitution of deuterium for $^1H$, wherein the deuterium(s) are selectively added to the molecule to alter the metabolism of the drug resulting in some enhanced property such as an increased half-life.

Methods of Treatment and Pharmaceutical Preparations and Compositions

Provided herein are methods for treating any of the disorders that are currently treated with antipsychotics, including by way of non-limiting example, schizophrenia, schizoaffective disorder, bipolar disorder, major depressive disorder (MDD), and autism, manic depressive disorder, depression with psychotic features, delusional disorder and other psychotic conditions, and the symptoms of hallucinations and delusions. Methods are provided herein for treating these disorders by administering to a subject in need thereof a first generation (i.e., typical) or a second generation (i.e., atypical) antipsychotic drug (e.g., a compound) in combination with a VMAT2 inhibitor. In certain embodiments, when the subject has developed a movement disorder (e.g., tardive dyskinesia) or has at least one symptom of a movement disorder, the methods comprising administering a VMAT2 inhibitor in combination with the antipsychotic are useful for treating the movement disorder (e.g., tardive dyskinesia). The VMAT2 inhibitor may prevent (i.e., reduce likelihood of occurrence of), slow progression of, delay, or treat a condition or disorder, such as a movement disorder.

As disclosed herein, surprisingly and unexpectedly, when an antipsychotic drug is administered in combination with a VMAT2 inhibitor for treating a neuropsychiatric disorder (e.g., schizophrenia, schizoaffective disorder, bipolar disorder, major depressive disorder (MDD), and autism, manic depressive disorder, depression with psychotic features, delusional disorder and other psychotic conditions, and the symptoms of hallucinations and delusions), the dose of the antipsychotic used in these methods is lower than (i.e., reduced, decreased, less than) the heretofore-described dosing range of the drug alone for effectively treating these disorders. In certain embodiments, the dose of the antipsychotic drug that is administered when combined with a VMAT2 inhibitor would not effectively treat the psychotic disorder if administered alone (i.e., if administered in the absence of the VMAT2 inhibitor). In other words, the combination of the VMAT2 inhibitor and the antipsychotic drug act synergistically in the treatment of the disorder. When used in combination with a VMAT2 inhibitor, an antipsychotic drug may be used at a dose that if administered alone would have little or no efficacy in treating the neuropsychiatric disorder, that is, the dose of the antipsychotic drug is subtherapeutic. That is, by combining a VMAT2 inhibitor with a subtherapeutic dose of the antipsychotic drug, the efficacy of the antipsychotic drug is enhanced. By way of example, treatment of the neuropsychiatric disorder or symptoms thereof may provide greater relief of anxiety and agitation when these are among the symptoms of the disorder.

Decreasing the dose of an antipsychotic drug has the beneficial effect of reducing the intensity of or preventing (i.e., decreasing the likelihood or risk of occurrence) one or more side effects of the antipsychotic drug. In one embodiment, such as when a typical antipsychotic drug is used for treating the disorder, the likelihood of occurrence of tardive dyskinesia and other tardive movement disorders may be reduced; the severity or intensity of the movement disorder may be decreased or lessened; or the frequency of occurrence of the movement disorder (or symptom thereof) may be reduced (i.e., decreased, lessened). In another embodiment, such as when an atypical drug is used in combination with a VMAT2 inhibitor for treating a neuropsychiatric disorder or symptoms thereof, the likelihood of occurrence or severity of a metabolic disturbance such as weight gain, glucose intolerance, and risk of atherosclerotic cardiovascular disease may be reduced. In other embodiments, side effects that may be reduced by administering to a subject in need thereof an anti-psychotic (either an atypical or typical antipsychotic) combined with a VMAT inhibitor include one or more of sedation, dry mouth, sexual dysfunction, and cardiac arrhythmias.

As understood by a person skilled in the medical art, the terms, "treat" and "treatment," refer to medical management of a disease, disorder, or condition of a subject (i.e., patient) (see, e.g., Stedman's Medical Dictionary). The terms "treatment" and "treating" embraces both preventative, i.e. prophylactic, or therapeutic, i.e. curative and/or palliative, treatment. Thus the terms "treatment" and "treating" comprise therapeutic treatment of patients having already developed the condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods described herein may be used, for instance, as therapeutic treatment over a period of time as well as for chronic therapy. In addition the terms "treatment" and "treating" comprise prophylactic treatment, i.e., a treatment of patients at risk to develop a condition mentioned hereinbefore, thus reducing the risk.

The subject in need of the compositions and methods described herein includes a subject who has been diagnosed by a person skilled in the medical and psychiatric arts with a neuropsychiatric disorder (e.g., schizophrenia, schizoaffective disorder, bipolar disorder, major depressive disorder (MDD), or autism). A subject (or patient) to be treated may be a mammal, including a human or non-human primate. The mammal may be a domesticated animal such as a cat or a dog.

Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the condition or disorder as well as subjects prone to have or at risk of developing the disease, condition, or disorder (e.g., schizophrenia or schizoaffective disorder, TD, or other conditions or disorders described herein), and those in which the disease, condition, or disorder is to be prevented (i.e., decreasing the likelihood of occurrence of the disease, disorder, or condition).

A "therapeutically effective amount" generally refers to an amount of a treatment, such as a antipsychotic drug and VMAT2 inhibitor, that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein. Optimal doses may generally be determined using experimental models and/or clinical trials. The optimal dose may depend upon the body mass, weight, or blood volume of the subject. In general, the dose range of a compound that is a VMAT2 inhibitor applicable per day is usually from 5.0 to 150 mg per day, and in certain embodiments from 10 to 100 mg per day. The dose of the VMAT2 inhibitor included in a composition or preparation also comprising an antipsychotic is sufficient to treat a movement disorder such as TD (i.e., the dose is a therapeutically effective dose for treating, preventing (i.e., reducing likelihood of occurrence of), slow progression of, delay the movement disorder).

Each of the antipsychotic and the VMAT2 inhibitor are administered at a time and frequency appropriate for treating a neuropsychiatric disorder, and the VMAT2 inhibitor is administered in a manner appropriate at a time and frequency appropriate for treating or preventing a movement disorder. The VMAT2 inhibitor may be administered 1, 2, or 3 times a day. The antipsychotic drug may be administered 1, 2, or 3 times a day independently or together with the VMAT2 inhibitor. In other embodiments, the antipsychotic is administered every week, every two weeks (approximately 2 times per month), every three weeks, every four weeks (approximately once per month), every 6 weeks, or every 8 weeks.

The oral dose range of typical and atypical antipsychotics applicable per day when administered alone (i.e., in the absence of a VMAT2 inhibitor) for an adult male schizophrenic subject may be found in Tables 1 and 2, in product inserts, or in the art. These recommended doses are sometimes augmented or reduced for different patient populations, such as for women, the elderly, children and adolescents, and for treatment of diseases other than schizophrenia. A person skilled in the medical/psychiatric art would therefore appreciate that the dose of a typical antipsychotic or an atypical antipsychotic that provides therapeutic benefit to a subject may need to be adjusted compared with the amounts shown in Table 1 and Table 2 depending on the gender, health status, age, presence of other medical or psychiatric conditions or diseases, route of administration, and formulation of drug administered, and other factors apparent to a person skilled in the art. As described herein, the dose of an antipsychotic drug administered to a subject may be significantly reduced compared with the amounts indicated in Table 1 and Table 2 and as described in the art when the antipsychotic drug is administered in combination with a VMAT2 inhibitor. The reduction in dose of the antipsychotic drug that is required to have antipsychotic therapeutic benefit when the drug is administered in combination with a VMAT2 inhibitor, (i.e., the subtherapeutic dose of the antipsychotic drug), may be adjusted as appropriate for a particular subject (e.g., gender, health status, age, presence of other medical or psychiatric conditions or diseases, route of administration, and formulation of drug administered, and other factors apparent to a person skilled in the art). In particular embodiments, the dose of the antipsychotic drug used in combination with a VMAT2 inhibitor may be at least about 10% less, at least about 20% less, at least about 25% less, at least about 30% less, at least about 35% less, at least about 40% less, at least about 45% less, at least about 50% less, at least about 55% less, at least about 60% less, at least about 65% less, at least about 70% less, at least about 75% less, at least about 80% less, at least about 85% less, or at least about 90% less than when used alone. In other certain embodiments, the dose of the antipsychotic drug when used in combination with a VMAT2 inhibitor may be between 10-90% less, 10-20% less, 10-25% less, 20-30% less, 25%-30% less, 25%-40% less, 25%-50% less, 25%-60% less, 25%-75% less, 25%-80% less, 30-40% less, 30-60% less, 40-50% less, 40-60% less, 50-60% less, 50-75% less, 60-70% less, 60-75% less, 70%-80% less, or 80-90% less than when the antipsychotic drug is used alone. As described herein examples of typical (i.e., first generation) antipsychotic drugs include fluphenazine, haloperidol, loxapine, molindone, perphenazine, pimozide, sulpiride, thioridazine, and trifluoperazine. Examples of atypical (i.e., second generation antipsychotic drugs include aripiprazole, asenapine, clozapine, iloperidone, olanzapine, paliperidone, quetiapine, risperidone, and ziprasidone.

The minimum dose that is sufficient to provide effective therapy and minimize toxicity is usually preferred. Subjects may generally be monitored for therapeutic effectiveness by clinical evaluation and psychiatric evaluation and by using assays suitable for the condition being treated or prevented, which assays will be familiar to those having ordinary skill in the art and are described herein. The level of a compound that is administered to a subject may be monitored by determining the level of the compound in a biological fluid, for example, in the blood, blood fraction (e.g., serum), and/or in the urine, and/or other biological sample from the subject. Any method practiced in the art to detect the compound may be used to measure the level of compound during the course of a therapeutic regimen.

The dose of a composition comprising an antipsychotic and a VMAT2 inhibitor described herein for treating schizophrenia or schizoaffective disorder or a related disease or disorder, TD, or other conditions or disorders described herein may depend upon the subject's condition, that is, stage of the disease, severity of symptoms caused by the disease, general health status, as well as age, gender, and weight, and other factors apparent to a person skilled in the medical and psychiatric arts. Similarly, the dose of each compound may be determined according to parameters understood by a person skilled in the art and as described herein.

The pharmaceutical compositions described herein that comprise at least one of the antipsychotic compounds and the pharmaceutical compositions described herein that comprise at least one of the VMAT2 inhibitor compounds described herein may be administered to a subject in need by any one of several routes that effectively deliver an effective amount of each compound. Such administrative routes include, for example, oral, parenteral, enteral, rectal, intranasal, buccal, sublingual, intramuscular, and transdermal. Compositions administered by these routes of administration and others are described in greater detail herein. The antipsychotic and the VMAT2 inhibitor when not formulated in the same composition may be administered by the same or different routes.

In certain embodiments, the VMAT2 inhibitor (or a physiologically or pharmaceutically acceptable salt thereof) and the antipsychotic drug (or a physiologically or pharmaceutically acceptable salt thereof) are formulated together to form a single composition. In other embodiments, a pharmaceutical preparation, referred to herein, comprises a pharmaceutical composition comprising an antipsychotic drug and a pharmaceutical composition comprising a VMAT2 inhibitor and, which may be referred to herein for convenience as a first pharmaceutical composition and a second pharmaceutical composition. The pharmaceutical compositions of the preparation may be administered concurrently or sequentially in either order to a subject to provide the desired therapeutic effect(s). As noted, reference to a "first pharmaceutical composition" and "a second pharmaceutical composition" is for convenience only and is not intended to describe an order of administration.

Each pharmaceutical preparation and pharmaceutical composition may further comprise at least one physiologically (or pharmaceutically) acceptable or suitable excipient. Any physiologically or pharmaceutically suitable excipient or carrier (i.e., a non-toxic material that does not interfere with the activity of the active ingredient(s)) known to those of ordinary skill in the art for use in pharmaceutical compositions may be employed in the compositions and preparations described herein. Exemplary excipients include diluents and carriers that maintain stability and integrity of the respective compound.

Pharmaceutically acceptable excipients are well known in the pharmaceutical art and described, for example, in Rowe et al., Handbook of Pharmaceutical Excipients: A Comprehensive Guide to Uses, Properties, and Safety, $5^{th}$ Ed., 2006, and in *Remington: The Science and Practice of Pharmacy* (Gennaro, $21^{st}$ Ed. Mack Pub. Co., Easton, Pa. (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used.

The pharmaceutical compositions may be in the form of a solution. The solution may comprise saline or sterile water, and may optionally include antioxidants, buffers, bacteriostats, and other common additives. Alternatively, they may be in the form of a solid, such as powder, tablets, pills, or the like. A composition comprising any one of the compounds described herein may be formulated for sustained or slow release. Such compositions may generally be prepared using well known technology and administered by, for example, oral, rectal or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

For oral formulations, at least one of the compounds described herein can be used alone or in combination with appropriate additives to make tablets, powders, granules or capsules, for example, dispersing and surface active agents; with conventional additives, such as lactose, mannitol, corn starch or potato starch; with binders; with disintegrators; with lubricants; and if desired, with diluents, buffering agents, moistening agents, preservatives, coloring agents, and flavoring agents. Compounds may be formulated with a buffering agent to provide for protection of the compound from low pH of the gastric environment and/or an enteric coating. A compound included in the compositions may be formulated for oral delivery with a flavoring agent, e.g., in a liquid, solid or semi-solid formulation and/or with an enteric coating. Oral formulations may be provided as gelatin capsules, which may contain the active compound along with powdered carriers, such as lactose, starch, cellulose derivatives, magnesium stearate, stearic acid, and the like. Similar carriers and diluents may be used to make compressed tablets.

Antipsychotics are commonly administered as oral compositions that are administered once or twice daily. Fast disintegrating buccal tablets and single dose injections have also been marketed. Long-acting medication has potential advantages over daily medication in improving compliance, thus reducing hospitalization and relapse rates. Intramuscular depot injections, generally providing 2 or 4 weeks of sustained efficacy, are available for aripiprazole, fluphenazine, haloperidol, olanzapine, paliperidone and risperidone. By way of non-limiting example, the antipsychotic drug can be administered according to the methods described herein on a once-daily or twice-daily schedule (or more if desired), typically with a single pill given each time. In certain specific embodiments, the antipsychotic drug and the VMAT2 inhibitor are formulated in the same tablet or pill for oral administration. In other embodiments, each of the VMAT2 inhibitor and the antipsychotic drug are formulated separately into different pills or tablets.

Also provided are kits that comprise one or more unit doses of each of the VMAT2 inhibitor and the antipsychotic drug. A non-limiting example of such a kit includes a blister pack. In another embodiment, the antipsychotic may be administered as a long-acting intramuscular injection and the VMAT2 inhibitor may be administered on a separate daily schedule.

In other embodiments, a preparation or composition that comprises an antipsychotic drug and a VMAT2 inhibitor further comprises one or more additional therapeutic agents, particularly therapeutic agents suitable for the treatment and/or prevention of the neuropsychiatric conditions and diseases described herein. Subjects who have a neuropsychiatric disorder, such as depression or bipolar disorder, are treated with multiple therapeutic drugs to control the symptoms of the disease. Additional therapeutic agents that may be suitable for combination with an antipsychotic drug and a VMAT2 inhibitor include, for example, one or more drugs useful for treating depression, bipolar disorder, or other disorders. Accordingly, in certain embodiments, a pharmaceutical preparation is provided that comprises an antipsychotic drug, or a physiologically acceptable salt thereof, and a VMAT2 inhibitor, or a physiologically acceptable salt thereof, and one or more additional therapeutic agents, optionally together with one or more pharmaceutically acceptable excipients, carriers, and/or diluents.

The following examples are provided for purposes of illustration, not limitation.

EXAMPLES

Example 1

Conditioned Avoidance Response Assay of Antipsychotic Activity for Risperidone, R,R,R-DHTBZ, and a Combination Thereof The conditioned avoidance response (CAR) test has been shown to be an effective and reliable preclinical model for assessing the antipsychotic activity of compounds. In the CAR paradigm, a rat is trained in a two chamber shuttle box to respond to a conditioned stimulus (auditory) by negative reinforcement. If the animal fails to move to the other chamber upon presentation of an auditory stimulus, a mild foot shock is applied to the side where the rat is located. The rat learns to avoid the mild foot shock by moving to the other chamber upon initiation of the auditory signal, termed a conditioned avoidance response. Crossing to the other chamber during administration of the shock is termed an escape response. If a rat fails to move to the other chamber even upon administration of the foot shock, the rat is considered to have an escape failure. Numerous studies have shown that typical and atypical antipsychotic drugs selectively suppress CAR, thus making it an ideal assay to screen potential antipsychotic compounds (see, e.g., Wadenberg et al., *Biobehav. Rev.* 1999. 23: 851-62).

Rats were trained every day for 3 to 4 weeks. In the training session, rats were placed in the CAR two-way shuttle box and the training period of 20 trials ensued. A trial consisted of a 10-sec presentation of an 80 dB white noise followed by a scrambled 0.6 mA foot shock lasting up to 20 sec. The inter-trial interval ranged from 20-60 sec. The rat learned to avoid shock by moving from one compartment to the other when the conditioned stimulus was presented (a conditioned avoidance response). A rat was deemed sufficiently trained if it avoided the shock when presented with the conditioned stimulus at least 19 times out of the 20 trials. Rats that did not pass these criteria were not used.

On test day, trained animals were acclimated in the test room for 30 minutes prior to testing. They were then dosed with compound and placed in the CAR two-way shuttle box. In the test, 20 trials were performed on each rat. In each trial the conditioned stimulus was applied (10-sec presentation of 80 dB white noise), followed by the foot shock (a scrambled 0.6 mA foot shock lasting up to 20 sec). If the animal moved to the other chamber on presentation of the conditioned stimulus, it was scored as a conditioned avoidance response. If it moved upon presentation of the foot shock, it was scored as an escape. If it failed to move upon presentation of the foot shock, it was scored as an escape failure. Antipsychotic efficacy is evident by an increase in the number of escapes. Data were analyzed by analysis of variance (ANOVA) followed by post-hoc comparisons with the Bonferroni Test when appropriate. An effect is considered significant if $p<0.05$. Outliers defined as two standard deviations above or below the mean were detected and were removed from all analysis. Results are reported as mean±SEM for number of escapes.

Animals: Male Wistar rats from Harlan (Indianapolis, Ind.) were used in the study. Upon receipt, rats were assigned unique identification numbers and were group housed with 3 rats per cage in polycarbonate cages with micro-isolator filter tops. All rats were examined, handled, and weighed prior to initiation of the study to assure adequate health and suitability. The rats were maintained at 12/12 light/dark cycle with lights on at 6:00 A.M. The room temperature was maintained between 20 and 23° C. with a relative humidity maintained around 50%. Chow and water were provided ad libitum for the duration of the study. For each test, animals were randomly assigned across treatment groups. Each treatment group contained 10 animals at time of testing.

Test Compounds: Risperidone (0.03, 0.1, 0.3, and 1 mg/kg) was dissolved in 10% DMSO and administered i.p. 30 min prior to testing at a dose volume of 1 ml/kg. (2R,3R,11bR)-3-isobutyl-9,10-dimethoxy-1,3,4,6,7,11b-hexahydro-2H-pyrido[2,1-a]isoquinolin-2-ol (called R,R,R-DHTBZ herein) (0.15 mg/kg) was dissolved in sterile water and administered p.o. 30 min prior to testing at a dose volume of 1 ml/kg and immediately following administration of risperidone or its vehicle. The vehicle control group received 10% DMSO (i.p., 30 min pretreatment, 1 ml/kg) immediately followed by administration of sterile water (p.o., 1 ml/kg).

Results: Risperidone (0.1 mg/kg) or R,R,R-DHTBZ (0.15 mg/kg) administered singly did not increase the number of escapes compared to vehicle. A combination of risperidone (0.1 mg/kg) and R,R,R-DHTBZ (0.15 mg/kg), at doses that showed no efficacy when administered alone, significantly increased the number of escapes compared to vehicle. This finding strongly suggests a synergistic effect on antipsychotic activity when the combination of risperidone and R,R,R-DHTBZ is administered.

Additionally, adding R,R,R-DHTBZ (0.15 mg/kg) to risperidone reduced the amount of risperidone needed to produce an antipsychotic effect. Administered singly, a dose of 0.3 mg/kg of risperidone was necessary to show antipsychotic efficacy in the CAR paradigm. The addition of R,R,R-DHTBZ (0.15 mg/kg) to risperidone resulted in antipsychotic activity at much lower doses of risperidone (0.03 and 0.1 mg/kg). This finding strongly suggests a synergistic effect of the combination on antipsychotic activity.

FIG. 1 shows a graph expressing the statistically significant marked increase of escapes in the conditioned avoidance test for the combination of the antipsychotic risperidone (0.1 mg/kg) in combination with the VMAT2 inhibitor R,R,R-DHTBZ (0.15 mg/kg). Risperidone (0.1 mg/kg) and R,R,R-DHTBZ (0.15 mg/kg) administered singly at the same doses as used in the combination did not result in changes from the vehicle results. These findings are strongly suggestive of antipsychotic activity due to the synergy of the combination.

Figure 2:
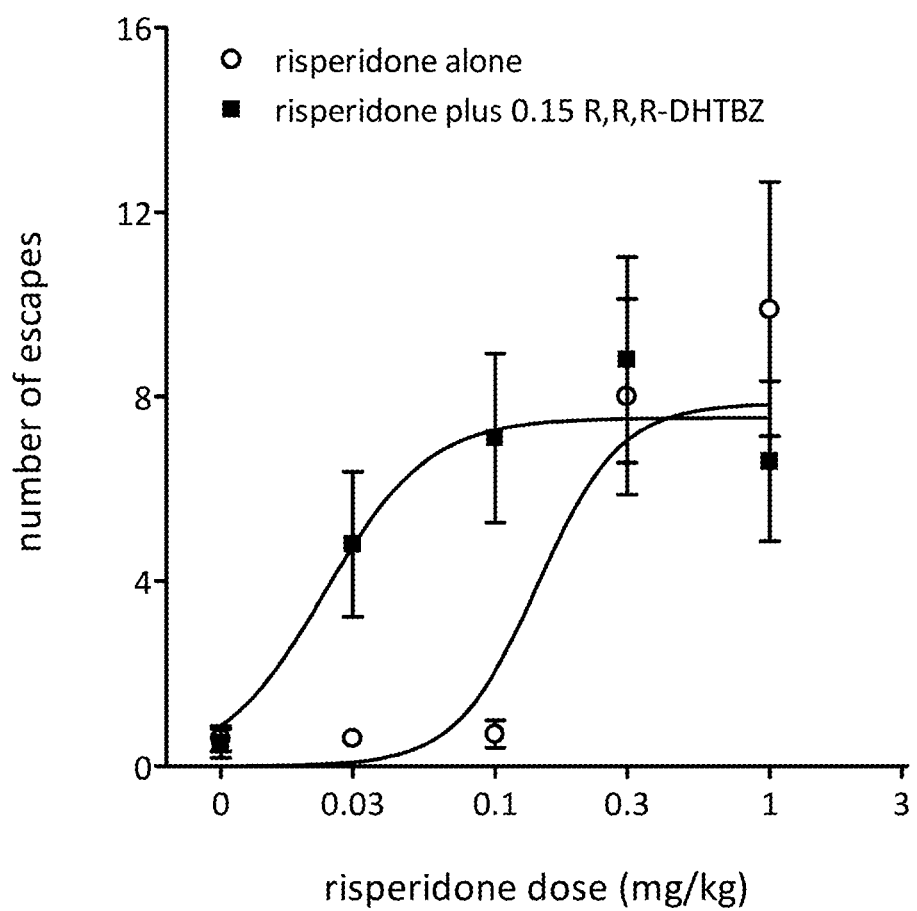
FIG. 2 shows the decrease in $ED_{50}$ (escape response) of the antipsychotic risperidone when administered in combination with the VMAT2 inhibitor R,R,R DHTBZ (0.15 mg/kg) in a rat model.

FIG. 2 shows a shift in $ED_{50}$ value for risperidone (0.03, 0.1, 0.3 and 1.0 mg/kg) dosed in combination with R,R,R-DHTBZ (0.15 mg/kg) as compared to risperidone (0.03, 0.1, 0.3 and 1.0 mg/kg) administered singly in rats. The $ED_{50}$ value of risperidone calculated from the fitted curve as the dose of compound required to produce 50% of the maximum response to compound decreased approximately 6-fold from a value of 0.14 mg/kg when risperidone was administered singly to 0.024 mg/kg when risperidone was administered in combination with the VMAT2 inhibitor R,R,R-DHTBZ (0.15 mg/kg). This 6-fold reduction corresponds to an 83% reduction of the risperidone dose. R,R,R DHTBZ (0.15 mg/kg) was similar to vehicle and showed no antipsychotic activity when administered singly. These findings are strongly suggestive of antipsychotic activity due to the synergy of the combination.

Example 2

Conditioned Avoidance Response Assay of Antipsychotic Activity for Olanzapine, R,R,R-DHTBZ, and a Combination Thereof The protocol of Example 1 was conducted with the atypical antipsychotic olanzapine and R,R,R-DHTBZ.

Test Compounds: Olanzapine (0.3, 0.6, 1 and 3 mg/kg) was dissolved in 10% DMSO and administered i.p. 30 min prior to testing at a dose volume of 1 ml/kg.

R,R,R-DHTBZ (0.15 mg/kg) was dissolved in sterile water and administered p.o. 30 min prior to testing at a dose volume of 1 ml/kg and immediately following administration of olanzapine or its vehicle. 10% DMSO (i.p., 30 min pretreatment, 1 ml/kg) immediately followed by administration of sterile water (p.o., 1 ml/kg) was used as the vehicle control group.

Results: Olanzapine (0.6 mg/kg) or R,R,R-DHTBZ (0.15 mg/kg) administered singly did not increase the number of escapes compared to vehicle. A combination of olanzapine (0.6 mg/kg) and R,R,R-DHTBZ (0.15 mg/kg), at doses which showed no efficacy when administered alone, significantly increased the number of escapes compared to vehicle. This finding strongly suggests a synergistic effect on antipsychotic activity due to the combination.

Additionally, adding R,R,R-DHTBZ (0.15 mg/kg) to olanzapine reduced the amount of olanzapine needed to produce an antipsychotic effect. Administered singly, a dose of 1 mg/kg of olanzapine was necessary to show antipsychotic efficacy in the CAR paradigm. The addition of R,R,R-DHTBZ (0.15 mg/kg) to olanzapine resulted in antipsychotic activity at a lower dose of olanzapine (0.6 mg/kg). This finding strongly suggests a synergistic effect on antipsychotic activity due to the combination.

Figure 3:
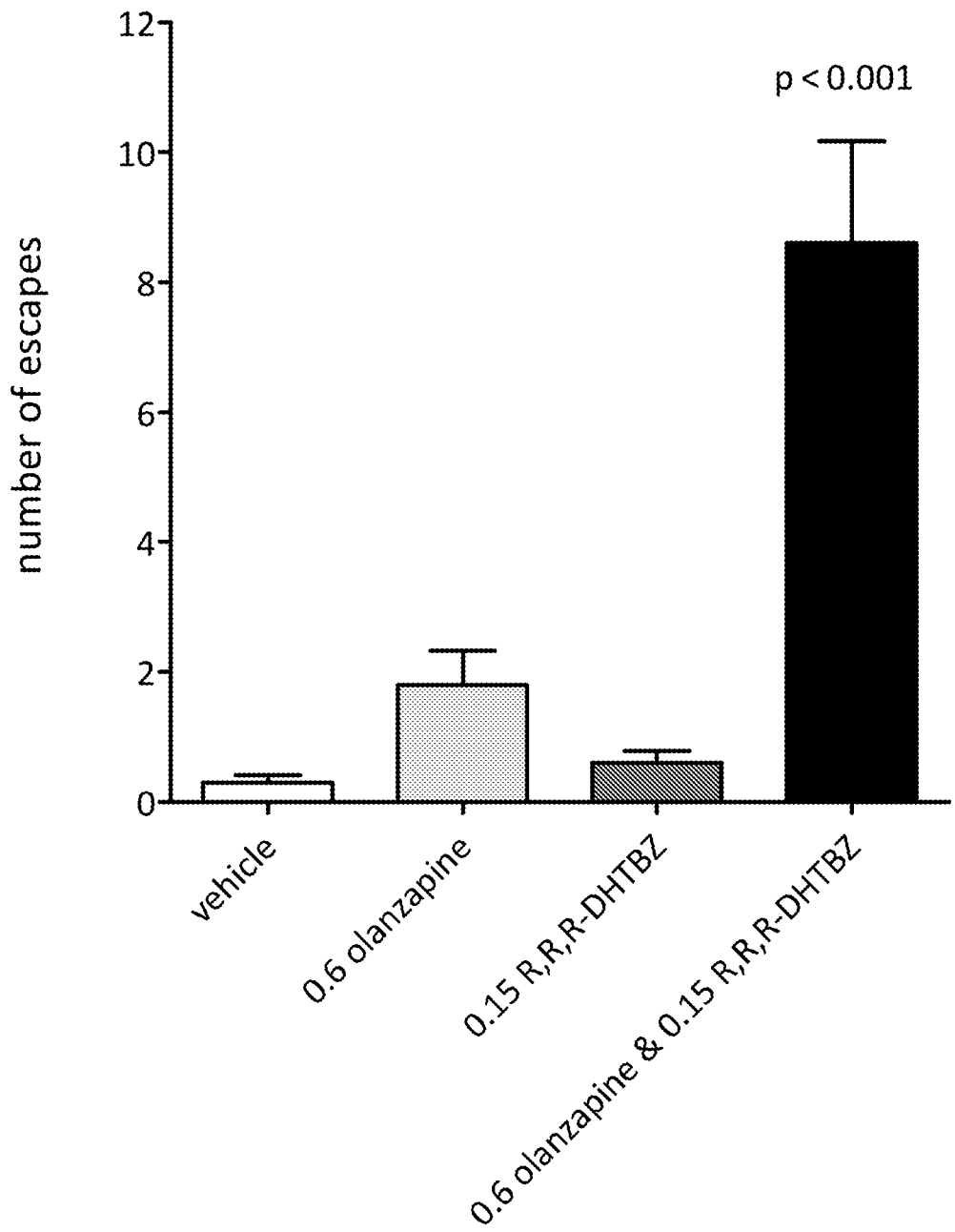
FIG. 3 shows the avoidance response in the Conditioned Avoidance Response (CAR) model as an indicator for antipsychotic activity. Vehicle, olanzapine singly (0.6 mg/kg), R,R,R DHTBZ singly, and a combination of olanzapine (0.6 mg/kg) and R,R,R DHTBZ (0.15 mg/kg) were administered and the number of escapes measured.

FIG. 3 shows a graph expressing the statistically significant marked increase of escapes in the conditioned avoidance test for the combination of the antipsychotic olanzapine (0.6 mg/kg) in combination with the VMAT2 inhibitor R,R,R-DHTBZ (0.15 mg/kg). Olanzapine (0.6 mg/kg) and R,R,R-DHTBZ (0.15 mg/kg) administered singly at the same doses as used in the combination did not result in changes from the vehicle results. These findings are strongly suggestive of antipsychotic activity due to the synergy of the combination.

Figure 4:
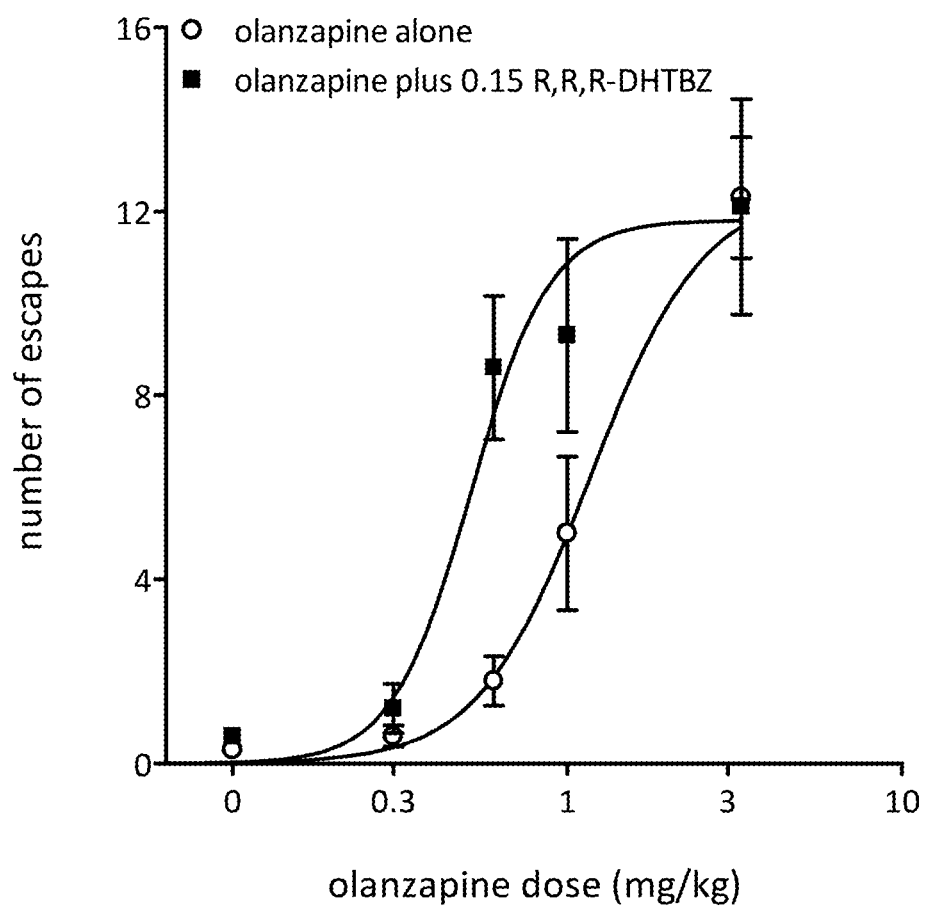
FIG. 4 illustrates the decrease in $ED_{50}$ (escape response) of the antipsychotic olanzapine when administered in combination with the VMAT2 inhibitor R,R,R DHTBZ (0.15 mg/kg) in a rat model.

FIG. 4 shows a shift in $ED_{50}$ value for olanzapine (0.3, 0.6, 1.0, and 3.0 mg/kg) dosed in combination with R,R,R-DHTBZ (0.15 mg/kg) as compared to olanzapine (0.3, 0.6, 1.0, and 3.0 mg/kg) administered singly in rats. The $ED_{50}$ value of olanzapine calculated from the fitted curve as the dose of compound required to produce 50% of the maximum response to compound decreased approximately 2-fold from a value of 1.2 mg/kg when olanzapine was administered singly to 0.51 mg/kg when olanzapine was administered in combination with the VMAT2 inhibitor R,R,R-DHTBZ (0.15 mg/kg). This 2-fold reduction corresponds to a 50% reduction of the olanzapine dose. These findings are strongly suggestive of antipsychotic activity due to the synergy of the combination.

Example 3

Conditioned Avoidance Response Assay of Antipsychotic Activity for Risperidone, Compound 5-1, and a Combination Thereof The protocol of Example 1 was conducted with the atypical antipsychotic risperidone and Compound 5-1 (see Example 5 for synthesis of Compound 5-1).

Test Compounds: Risperidone (0.1, 0.3, and 1 mg/kg) was dissolved in 10% DMSO and administered i.p. 30 min prior to testing at a dose volume of 1 ml/kg. Compound 5-1 (0.3 mg/kg) was dissolved in sterile water and administered p.o. 60 min prior to testing at a dose volume of 1 ml/kg, that is, 30 min before administration of risperidone or its vehicle. The vehicle control group received sterile water (p.o., 1 ml/kg) followed 30 min later by administration of 10% DMSO (i.p., 30 min pretreatment, 1 ml/kg).

Results: Risperidone (0.1 mg/kg) or Compound 5-1 (0.3 mg/kg) administered singly did not increase the number of escapes compared to vehicle. A combination of risperidone (0.1 mg/kg) and Compound 5-1 (0.3 mg/kg), at doses which showed no efficacy when administered alone, significantly increased the number of escapes compared to vehicle. This finding strongly suggests a synergistic effect on antipsychotic activity when the combination of risperidone and Compound 5-1 is administered.

Additionally, adding Compound 5-1 (0.3 mg/kg) to risperidone reduced the amount of risperidone needed to produce an antipsychotic effect. Administered singly, a dose of 0.3 mg/kg of risperidone was necessary to show antipsychotic efficacy in the CAR paradigm. The addition of Compound 5-1 (0.3 mg/kg) to risperidone resulted in antipsychotic activity at much lower doses of risperidone (0.1 mg/kg). This finding strongly suggests a synergistic effect of the combination on antipsychotic activity.

Figure 5:
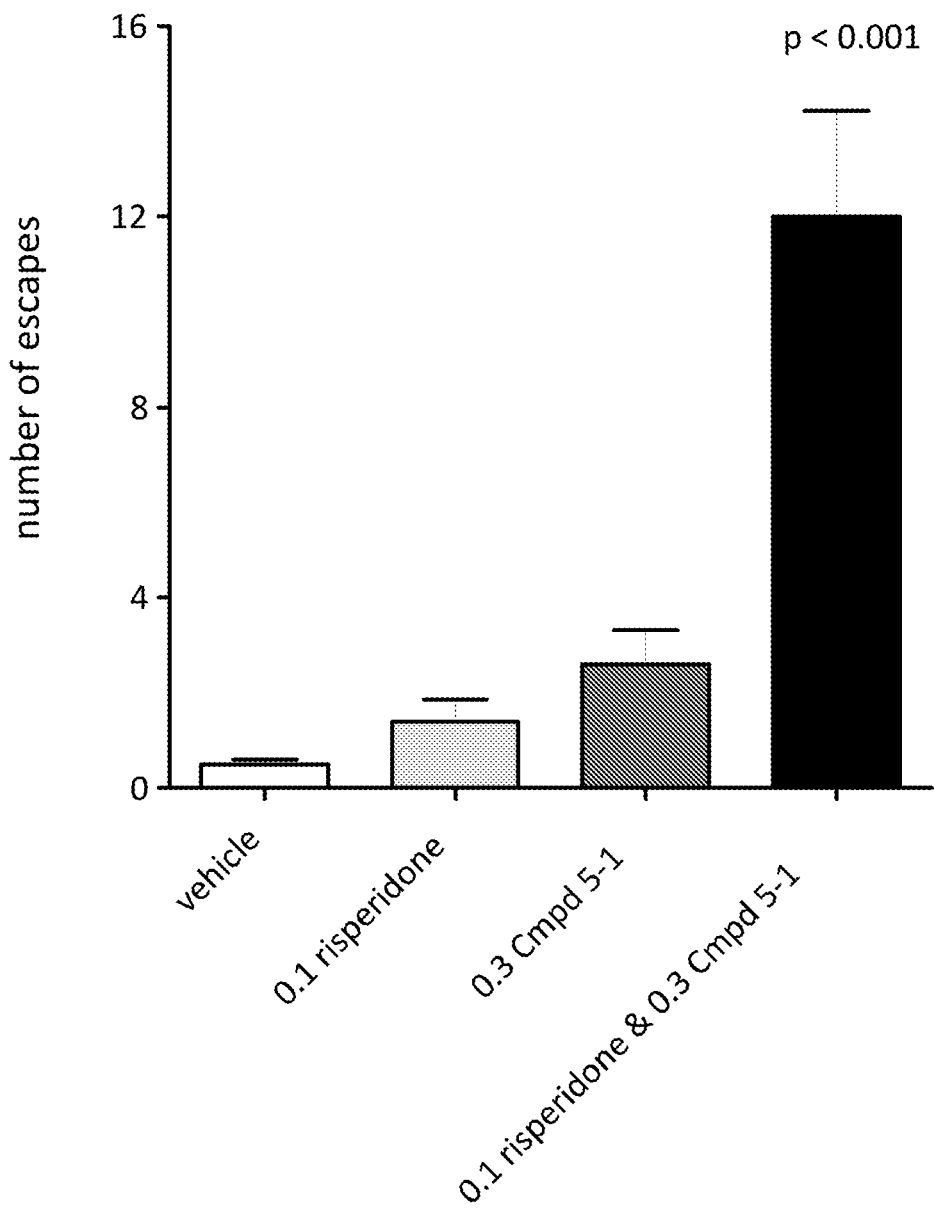
FIG. 5 shows the number of escapes in the Conditioned Avoidance Response (CAR) model as an indicator for antipsychotic activity. Vehicle, risperidone (0.1 mg/kg) singly, Compound 5-1 singly (0.3 mg/kg), and a combination of risperidone 0.1 mg/kg) and Compound 5-1 (0.3 mg/kg) (Cmpd 5-1) were administered and the number of escapes measured.

FIG. 5 shows a graph expressing the statistically significant marked increase of escapes in the conditioned avoidance test for the combination of the antipsychotic risperidone (0.1 mg/kg) in combination with the VMAT2 inhibitor Compound 5-1 (0.3 mg/kg). Risperidone (0.1 mg/kg) and Compound 5-1 (0.3 mg/kg) administered singly at the same doses as used in the combination did not result in changes from the vehicle results. These findings are strongly suggestive of antipsychotic activity due to the synergy of the combination.

Figure 6:
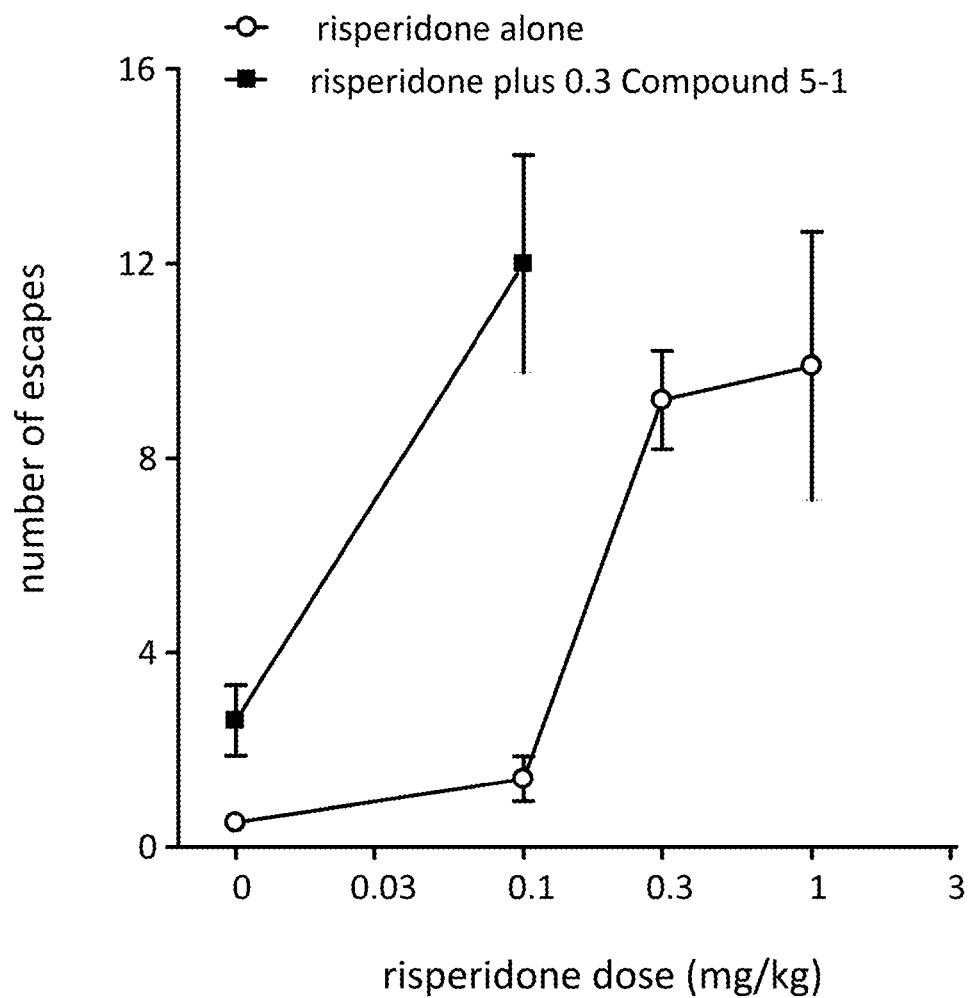
FIG. 6 shows the decrease in $ED_{50}$ (escape response) of the antipsychotic risperidone when administered in combination with the VMAT2 Compound 5-1 (0.3 mg/kg) in a rat model.

FIG. 6 shows a shift in the dose of risperidone (0.1 mg/kg) dosed in combination with Compound 5-1 (0.3 mg/kg) as compared to risperidone (0.1, 0.3 and 1.0 mg/kg) administered singly in rats. The dose of risperidone calculated from the fitted line as the dose of compound required to produce 8 escapes decreased approximately 7-fold from a value of 0.26 mg/kg when risperidone was administered singly to 0.038 mg/kg when risperidone was administered in combination with the VMAT2 inhibitor, Compound 5-1 (0.3 mg/kg). This 7-fold reduction corresponds to an 86% reduction of the risperidone dose. Compound 5-1 (0.3 mg/kg) was similar to vehicle and showed no antipsychotic activity when administered singly. These findings are strongly suggestive of antipsychotic activity due to the synergy of the combination.

Example 4

Conditioned Avoidance Response Assay of Antipsychotic Activity for Olanzapine, Compound 5-1, and a Combination Thereof The protocol described in Examples 1 and 2 was conducted with the atypical antipsychotic olanzapine and Compound 5-1 (see Example 5).

Test Compounds: Olanzapine (0.6, 1 and 3 mg/kg) was dissolved in 10% DMSO and administered i.p. 30 min prior to testing at a dose volume of 1 ml/kg. Compound 5-1 (0.3 mg/kg) was dissolved in sterile water and administered p.o. 60 min prior to testing at a dose volume of 1 ml/kg, that is, 30 min before administration of olanzapine or its vehicle. The vehicle control group received sterile water (p.o., 1 ml/kg) followed 30 min later by administration of 10% DMSO (i.p., 30 min pretreatment, 1 ml/kg).

Results: Olanzapine (0.6 mg/kg) or Compound 5-1 (0.3 mg/kg) administered singly did not increase the number of escapes compared to vehicle. A combination of olanzapine (0.6 mg/kg) and Compound 5-1 (0.3 mg/kg), at doses which showed no efficacy when administered alone, significantly increased the number of escapes compared to vehicle. This finding strongly suggests a synergistic effect on antipsychotic activity when the combination of olanzapine and Compound 5-1 is administered.

Additionally, combining Compound 5-1 (0.3 mg/kg) with olanzapine reduced the amount of olanzapine needed to produce an antipsychotic effect. Administered singly, a dose of 1 mg/kg of olanzapine was necessary to show antipsychotic efficacy in the CAR paradigm. The addition of Compound 5-1 (0.3 mg/kg) to olanzapine resulted in antipsychotic activity at a lower dose of olanzapine (0.6 mg/kg). This finding strongly suggests a synergistic effect of the combination on antipsychotic activity.

Figure 7:
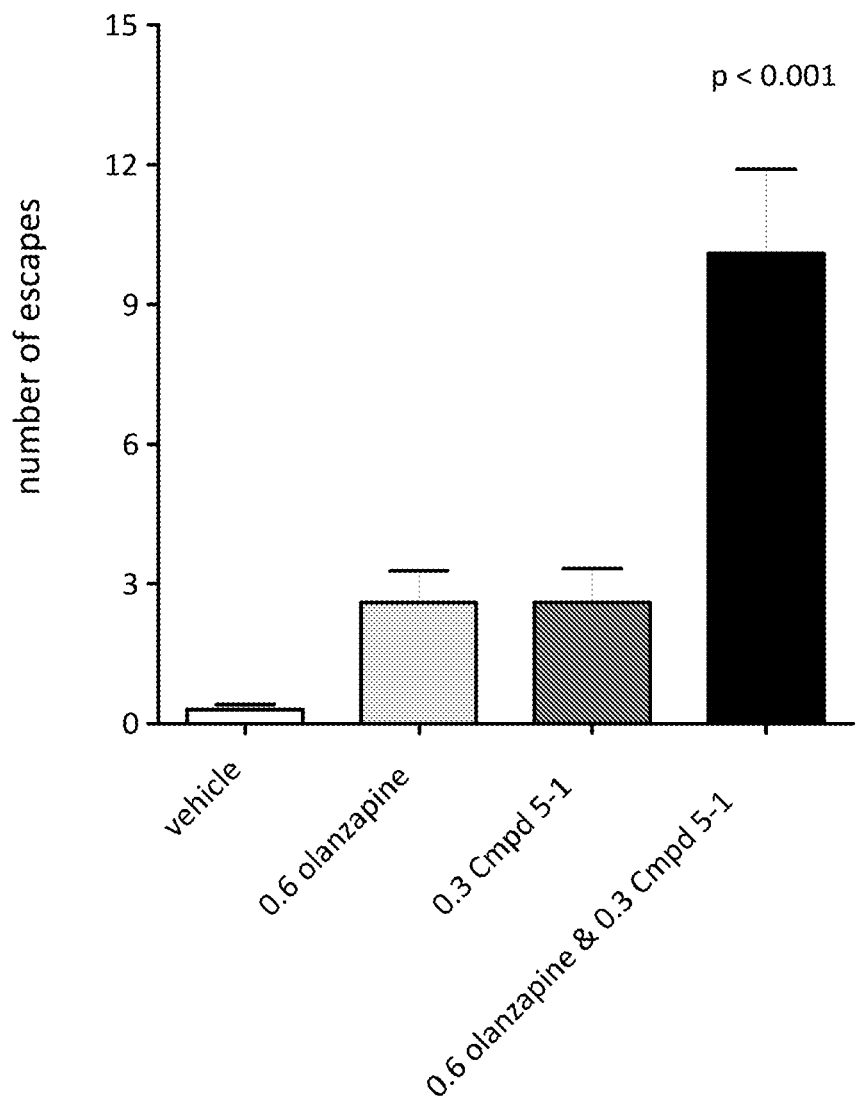
FIG. 7 shows the avoidance response in the Conditioned Avoidance Response (CAR) model as an indicator for antipsychotic activity. Vehicle, olanzapine singly (0.6 mg/kg), Compound 5-1 (0.3 mg/kg) (Cmpd 5-1) singly, and a combination of olanzapine (0.6 mg/kg) and Compound 5-1 (0.3 mg/kg) were administered and the number of escapes measured.

FIG. 7 shows a graph expressing the statistically significant marked increase of escapes in the conditioned avoidance test for the combination of the antipsychotic olanzapine (0.6 mg/kg) in combination with the VMAT2 inhibitor, Compound 5-1 (0.3 mg/kg). Olanzapine (0.6 mg/kg) and Compound 5-1 (0.3 mg/kg) administered singly at the same doses as used in the combination did not result in changes from the vehicle results. These findings are strongly suggestive of antipsychotic activity due to the synergy of the combination.

Figure 8:
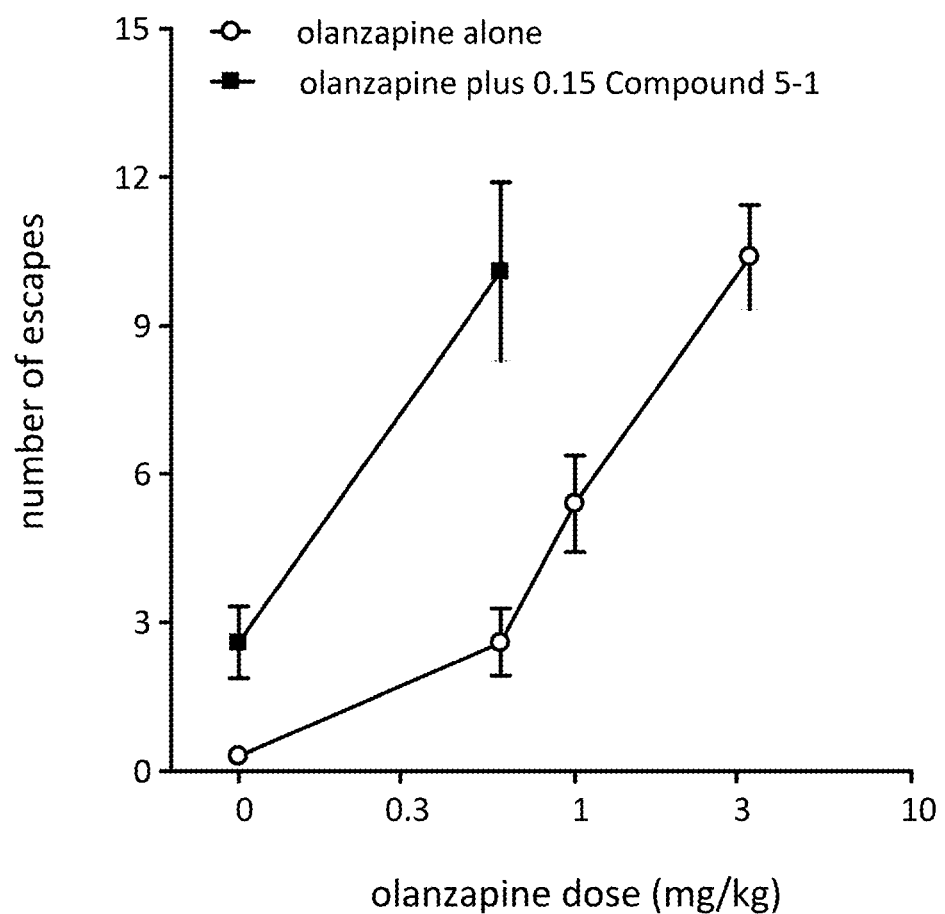
FIG. 8 illustrates the decrease in $ED_{50}$ (escape response) of the antipsychotic olanzapine when administered in combination with the VMAT2 inhibitor Compound 5-1 (0.3 mg/kg) in a rat model.

FIG. 8 shows a shift in the dose of olanzapine (0.6 mg/kg) dosed in combination with Compound 5-1 (0.3 mg/kg) as compared to olanzapine (0.6, 1 and 3 mg/kg) administered singly in rats. The dose of olanzapine calculated from the fitted line as the dose of compound required to produce 5 escapes decreased approximately 7-fold from a value of 0.93 mg/kg when olanzapine was administered singly to 0.18 mg/kg when olanzapine was administered in combination with the VMAT2 inhibitor Compound 5-1 (0.3 mg/kg). This 5-fold reduction corresponds to an 80% reduction of the olanzapine dose. Compound 5-1 (0.3 mg/kg) was similar to vehicle and showed no antipsychotic activity when administered singly. These findings are strongly suggestive of antipsychotic activity due to the synergy of the combination.

Example 5

[(2R,3S,11BR)-9,10-Dimethoxy-3-(2-Methylpropyl)-1H,2H,3H,4H,6H,7H,11BH-Pyrido[2,1-A]Isoquinolin-2-yl]Methanol

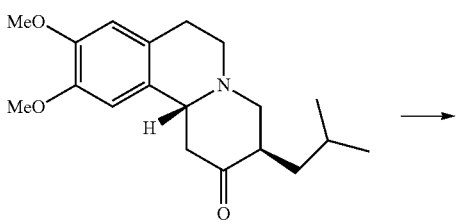

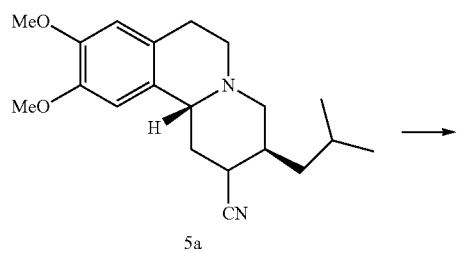

5a

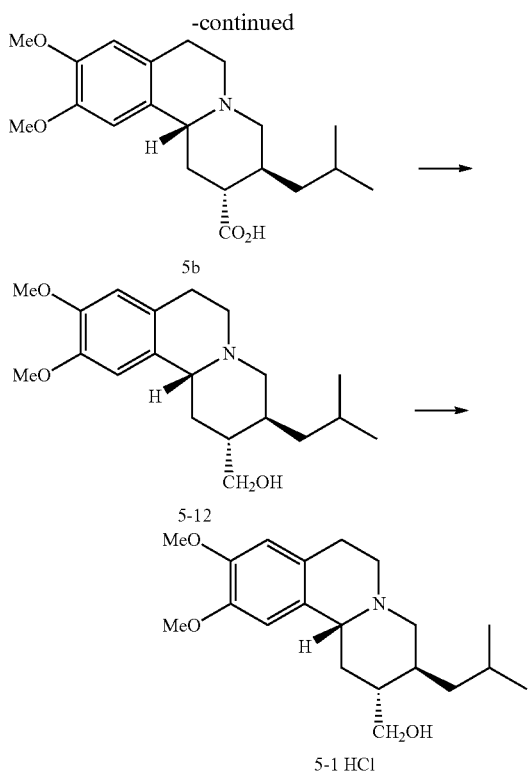

Step 5A: (3S,11bR)-9,10-Dimethoxy-3-(2-methyl-propyl)-1H,2H,3H,4H,6H,7H,11bH-pyrido[2,1-a]isoquinoline-2-carbonitrile To a 3 L 3-neck round bottomed flask DMSO (1.1 L) and TOSMIC (104 g, 532.5 mmol, 1.3 eq) were charged. To this mixture KO-t-Bu (119.5 g, 1.065 mol) was charged at once at ambient temp (22° C.). An exotherm was observed and the temperature of the mixture increased to 39° C. Then a suspension of tetrabenazine (130 g, 410 mmol) in DMSO (500 mL) was added to the reaction mixture slowly over 25 min (a slight exotherm observed). EtOH (10.5 mL) was added to this mixture, and the mixture was stirred at ambient temp for 3 h. LC-MS analysis of the mixture revealed presence of ~4:1 ratio of 5a and starting material. The mixture was poured into cold water (9 L). The mixture was then extracted with EtAOc (4 L). The aqueous layer was extracted with EtOAc (2 L). The combined organics were washed with brine (2 L), dried over $Na_2SO_4$ and concentrated. The residue was dissolved in acetone (200 ml) and loaded onto a silica column (2 Kg silica gel, packed with hexanes). The column was eluted first with hexanes (2.5 L), followed by 5-20% of acetone in hexanes. The fractions containing 5a and other impurities were combined and concentrated to give an orange oil (72 g), which was dissolved in acetone (100 ml) and loaded onto a silica column (1 Kg silica gel, packed with hexanes). The column was eluted first with hexanes (1 L), followed by 5% of acetone in hexanes (2 L), 10% of acetone in hexanes (2 L), 15% of acetone in hexanes (2 L), and 20% of acetone in hexanes (2 L). The fractions containing >90% purity were combined and concentrated to give (3S,11bR)-9,10-dimethoxy-3-(2-methylpropyl)-1H,2H,3H,4H,6H,7H,11bH-pyrido[2,1-a]isoquinoline-2-carbonitrile 5a as an orange solid (61 g, m/z 329.2 [MH+]). The fractions containing a mixture of 5a and starting material were collected and concentrated to give 48 g of material, which was dissolved in DMSO (50 ml) and was added to a mixture of TOSMIC (25 g) and KO-t-Bu (28.7 g) in DMSO (250 ml) as shown above. The residue was dissolved in acetone (10 ml) and loaded onto a silica column (600 g silica gel, packed with hexanes). The column was eluted first with hexanes (800 ml), followed by 5-20% of acetone in hexanes. The fractions containing product were combined and concentrated to give orange solid 5a (33 g).

Step 5B: (3S,11bR)-9,10-Dimethoxy-3-(2-methyl-propyl)-1H,2H,3H,4H,6H,7H,11bH-pyrido[2,1-a]isoquinoline-2-carboxylic acid A 1 gallon pressure reactor was charged with a suspension of 5a (94 g, 286 mmol) in methanol (940 ml) and NaOH (343 g, 8.6 mol) in water (940 ml). This mixture was stirred at 120° C. (internal temp) for 67 h. The mixture was cooled to room temperature and transferred to a round bottom flask. The mixture was concentrated in a rotavap to ~1 L. The mixture was then adjusted pH to 7 using aqueous 6N HCl under cooling. The mixture was extracted with DCM (2×3 L and 1×2 L). The combined organics were dried over $Na_2SO_4$ and concentrated to give a dark residue (88 g). The dark residue was taken in acetonitrile (500 ml) and stirred for 30 min. The mixture was filtered and the solid was washed with acetonitrile (50 ml). The solid was dried under vacuum for 2 hours to afford light brown solid (42 g, 49%). This solid was combined with the filtrate and concentrated to a residue. The residue was dissolved in DCM (150 ml) and loaded onto a silica column packed with DCM. The column was eluted with 0-25% of methanol in DCM. The fractions containing product were combined and concentrated to give (3S,11bR)-9,10-Dimethoxy-3-(2-methylpropyl)-1H,2H,3H,4H,6H,7H,11bH-pyrido[2,1-a]isoquinoline-2-carboxylic acid 5b as a pale brown solid (71 g, 71% yield, 92% purity, m/z 348.2 [MH+]).

Step 5C: [(2R,3S,11bR)-9,10-Dimethoxy-3-(2-methylpropyl)-1H,2H,3H,4H,6H,7H,11bH-pyrido[2,1-a]isoquinolin-2-yl]methanol A 3 round bottom flask was charged with 5b (73.5 g, 211.5 mmol) and THF (1.48 L). This mixture was stirred and cooled to 10° C. (internal temp). To this mixture was added 1 M LAH in THF (423 ml, 423 mmol) slowly over 20 min keeping the temp below 20° C. The cooling bath was removed, and the mixture was warmed up to room temp. The mixture was heated to 55° C. and stirred for 30 min. The mixture was cooled to room temp and then to 10° C. EtOAc (30 ml) was added slowly to quench un-reacted LAH followed by ethanol (30 ml). Then water (150 ml) was added to this mixture. The mixture was then concentrated to remove most of organic solvents. Then the mixture was diluted with water (700 ml) and DCM (1 L). The suspension was filtered through a pad of celite. The filtered cake was washed with DCM (2×500 ml). The combined filtrates were taken in separatory funnel and the layers separated. The aqueous layer was extracted with DCM (1 L). The combined organics were dried over $Na_2SO_4$ and concentrated to give a dark residue. The residue was chromatographed on silica column using 0-10% of methanol in DCM as eluent. The fractions containing product were combined and concentrated to afford foamy orange residue. To this residue hexanes (100 ml) was added and concentrated under reduced pressure at 45° C. for 2 h to afford [(2R,3S,11bR)-9,10-

Dimethoxy-3-(2-methylpropyl)-1H,2H,3H,4H,6H,7H, 11bH-pyrido[2,1-a]isoquinolin-2-yl]methanol (5-1) (also called Compound 5-1 herein) as a pale brown solid (51 g, 72%, 95% HPLC purity by 220 nm, m/z 334.2 [MH$^+$]). This material may be further purified by silica gel chromatography using 0-10% of methanol in DCM or ethyl acetate as eluent.

Step 5D: [(2R,3S,11bR)-9,10-Dimethoxy-3-(2-methylpropyl)-1H,2H,3H,4H,6H,7H,11bH-pyrido[2,1-a]isoquinolin-2-yl]methanol HCl salt A 2 L roundbottom flask was charged with 5-1 (43 g, 129 mmol) and diethyl ether (860 mL). This mixture was stirred and cooled to 15° C. (internal temp). To this mixture was added 2 M HCl in diethyl ether (97 ml, 193 mmol) slowly over 15 min. A white precipitate formed. The cooling bath was removed and the mixture was warmed to room temp. The mixture was then stirred for 45 min. The mixture was filtered and the filtered solid was washed with diethyl ether (100 ml), with MTBE (100 ml) and then with hexanes (100 ml). The solid was then dried in vacuum oven at 40° C. for 18 h. [(2R,3S,11bR)-9,10-Dimethoxy-3-(2-methylpropyl)-1H,2H,3H,4H,6H,7H,11bH-pyrido[2,1-a]isoquinolin-2-yl]methanol HCl salt (5-1 HCl) was isolated as an off-white solid (44.7 g, 94% yield, m/z 334.2 [MH$^+$]).

Example 6

Methods for Determining VMAT2 Inhibitory Activity of a Compound

Examples of techniques for determining the capability of a compound to inhibit VMAT2 are provided below.

The procedure is adapted from that described previously (see, e.g., Near, (1986), *Mol. Pharmacol.* 30: 252-57; Teng, et al., *J. Neurochem.* 71, 258-65, 1998). Homogenates from human platelets or Sprague-Dawley rat forebrain were prepared by homogenization and then washed by centrifugation as described previously (see, e.g., Hoare et al., (2003) *Peptides* 24:1881-97). In a total volume of 0.2 mL in low-binding 96-well plates (Corning #3605), twelve concentrations of Compound 5-1 and R,R,R-DHTBZ were competed against 6 nM $^3$H-dihydrotetrabenazine (American Radiolabeled Chemicals, Kd 2.6 nM) on rat forebrain homogenate (100 µg membrane protein per well) or human platelet homogenate (50 µg membrane protein per well) in VMAT2 binding buffer (Dulbecco's phosphate buffered saline, 1 mM EDTA, pH 7.4). Following incubation at 25° C. for two hours, bound radioligand was collected by rapid filtration onto GF/B glass fiber filters using a Unifilter-96 Harvester (PerkinElmer). Filter plates were pre-treated for 10 minutes with 0.1% polyethylenimine, and following harvesting the filter plates were washed with 800 µl VMAT2 binding buffer. Bound radioligand was quantified by scintillation counting using a Topcount NXT (PerkinElmer). The results of the competition binding studies are presented below in Table 3 and Table 4.

TABLE 3

Rat Forebrain VMAT2 Affinity from Competition Binding Studies

| Compound | pKi (n) | Ki (nM) |
|---|---|---|
| Compound 5-1 | 8.6 ± 0.1 (2) | 2.6 |
| R,R,R-DHTBZ | 8.7 ± 0.2 (6) | 1.9 |

TABLE 4

Human Platelet VMAT2 Affinity from Competition Binding Studies

| Compound | pKi (n) | Ki (nM) |
|---|---|---|
| Compound 5-1 | 8.3 ± 0.1 (2) | 5.2 |
| R,R,R-DHTBZ | 8.6 ± 0.3 (3) | 2.6 |

Another technique that may be routinely performed to determine the capability of a compound to inhibit VMAT2 is provided below. The following procedure is adapted from a previously described method (see Teng, et al., *J. Neurochem.* 71, 258-65, 1998).

Preparation of rat striatal vesicles: Rat striata from three rats are pooled and homogenized in 0.32 M sucrose. The homogenate is then centrifuged at 2,000×g for 10 min at 4° C. and the resulting supernatant is centrifuged at 10,000×g for 30 min at 4° C. The resulting pellet containing the enriched synaptosomal fraction (2 mL) is subjected to osmotic shock by addition of 7 mL of distilled H$_2$O, and subsequently the suspension is homogenized. The osmolarity is restored by the addition of 0.9 mL of 0.25 M HEPES and 0.9 mL of 1.0 M neutral L-(+)-tartaric acid dipotassium salt buffer (pH 7.5), followed by a 20 min centrifugation (20,000×g at 4° C.). The supernatant is then centrifuged for 60 min (55,000×g at 4° C.) and the resulting supernatant is centrifuged for 45 min (100,000×g at 4° C.). The resulting pellet is resuspended in 25 mM HEPES, 100 mM L-(+)-tartaric acid dipotassium salt, 5 mM MgCl$_2$, 10 mM NaCl, 0.05 mM EGTA, pH 7.5 to a protein concentration of 1-2 mg/mL and stored at −80° C. for up to 3 weeks without appreciable loss of binding activity. Immediately before use, the final pellet is resuspended in binding buffer (25 mM HEPES, 100 mM L-(+)-tartaric acid dipotassium salt, 5 mM MgCl$_2$, 10 mM NaCl, 0.05 mM EGTA, 0.1 mM EDTA, 1.7 mM ascorbic acid, pH 7.4).

[$^3$H]-dihydrotetrabenazine (DHTBZ) Binding: Aliquots of the vesicle suspension (0.16 mL, 15 µg of protein/mL) are incubated with competitor compounds (ranging from 10$^{-6}$ to 10$^{-12}$ M) and 2 nM [$^3$H]-dihydrotetrabenazine (HTBZ; specific activity: 20 Ci/mmol, American Radiolabeled Chemicals, Inc.) for 1 h at room temperature in a total volume of 0.5 mL. The reaction is terminated by rapid filtration of the samples onto Whatman GF/F filters using a Brandel cell harvester. Nonspecific binding is determined using 20 µM tetrabenazine (TBZ). Filters are previously soaked for 2 h with ice-cold polyethyleneimine (0.5%). After the filters are washed three times with the ice-cold buffer, they are placed into scintillation vials with 10 mL scintillation cocktail. Bound radioactivity is determined by scintillation spectrometry.

The various embodiments described herein can be combined to provide further embodiments. Described herein are the following exemplary embodiments.

Embodiment 1. A method for treating a neuropsychiatric disorder in a subject comprising administering to the subject (a) an antipsychotic drug and (b) a VMAT2 inhibitor, wherein the therapeutically effective amount of the antipsychotic drug administered to the subject is less than the therapeutically effective amount of the antipsychotic drug when administered in the absence of the VMAT2 inhibitor.

Embodiment 2. The method of Embodiment 1 wherein the neuropsychiatric disorder is schizophrenia, schizoaffective disorder, bipolar disorder, major depressive disorder (MDD), or autism.

Embodiment 3. The method of Embodiment 1 or Embodiment 2 wherein the antipsychotic drug and the VMAT2 inhibitor are administered concurrently.

Embodiment 4. The method of any one of Embodiments 1-3 wherein the antipsychotic drug and the VMAT2 inhibitor are formulated in the same pharmaceutical composition.

Embodiment 5. The method of any one of Embodiments 1-3 wherein the antipsychotic drug is formulated in a first pharmaceutical composition and the VMAT2 inhibitor is formulated in a second pharmaceutical composition.

Embodiment 6. The method of any one of Embodiments 1-5 wherein the antipsychotic drug is a typical antipsychotic drug.

Embodiment 7. The method of Embodiment 6 wherein the typical antipsychotic drug is fluphenazine, haloperidol, loxapine, molindone, perphenazine, pimozide, sulpiride, thioridazine, or trifluoperazine.

Embodiment 8. The method of any one of Embodiments 1-5 wherein the antipsychotic drug is an atypical antipsychotic drug.

Embodiment 9. The method of Embodiment 8 wherein the atypical antipsychotic drug is aripiprazole, asenapine, clozapine, iloperidone, olanzapine, paliperidone, quetiapine, risperidone, or ziprasidone.

Embodiment 10. The method of any one of Embodiments 1-9 wherein the therapeutically effective amount of the antipsychotic drug is 10 to 90% less than the therapeutically effective amount of the antipsychotic drug when administered in the absence of the VMAT2 inhibitor.

Embodiment 11. The method of any one of Embodiments 1-9 wherein the therapeutically effective amount of the antipsychotic drug is at least 25% less than the therapeutically effective amount of the antipsychotic drug when administered in the absence of the VMAT2 inhibitor.

Embodiment 12. The method of any one of Embodiments 1-9 wherein the therapeutically effective amount of the antipsychotic drug is at least 50% less than the therapeutically effective amount of the antipsychotic drug when administered in the absence of the VMAT2 inhibitor.

Embodiment 13. The method of any one of Embodiments 1-12 wherein the VMAT2 inhibitor is tetrabenazine (3-isobutyl-9,10-dimethoxy-1,3,4,6,7,11b-hexahydro-2H-pyrido[2,1-a]isoquinolin-2-one).

Embodiment 14. The method of any one of Embodiments 1-12 wherein the VMAT2 inhibitor is (2R,3R,11bR)-3-isobutyl-9,10-dimethoxy-1,3,4,6,7,11b-hexahydro-2H-pyrido[2,1-a]isoquinolin-2-ol (R,R,R DHTBZ), or a precursor thereof.

Embodiment 15. The method of any one of Embodiments 1-12, wherein the VMAT2 inhibitor is (S)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester.

Embodiment 16. The method of any one of Embodiments 1-12, wherein the VMAT2 inhibitor is [(2R,3S,11bR)-9,10-Dimethoxy-3-(2-methylpropyl)-1H,2H,3H,4H,6H,7H,11bH-pyrido[2,1-a]isoquinolin-2-yl]methanol, or a precursor thereof.

Embodiment 17. The method of any one of Embodiments 1-12, wherein the VMAT2 inhibitor is 3-isobutyl-9,10-$d_6$-dimethoxy-1,3,4,6,7,11b-hexahydro-2H-pyrido[2,1-a]isoquinolin-2-one ($d_6$-TBZ).

Embodiment 18. A pharmaceutical preparation for use in treating a neuropsychiatric disorder, said preparation comprising an antipsychotic drug and a VMAT2 inhibitor, wherein the preparation comprises an amount of the antipsychotic drug that is a subtherapeutic amount if used in the absence of the VMAT2 inhibitor.

Embodiment 19. The pharmaceutical preparation of Embodiment 18 wherein the neuropsychiatric disorder is schizophrenia, schizoaffective disorder, bipolar disorder, major depressive disorder (MDD), or autism.

Embodiment 20. The pharmaceutical preparation of Embodiment 18 or Embodiment 19, wherein the antipsychotic drug is a typical antipsychotic drug.

Embodiment 21. The pharmaceutical preparation of Embodiment 20 wherein the typical antipsychotic drug is fluphenazine, haloperidol, loxapine, molindone, perphenazine, pimozide, sulpiride, thioridazine, or trifluoperazine.

Embodiment 22. The pharmaceutical preparation of Embodiment 18 or Embodiment 19 wherein the antipsychotic drug is an atypical antipsychotic drug.

Embodiment 23. The pharmaceutical preparation of Embodiment 22, wherein the atypical antipsychotic drug is aripiprazole, asenapine, clozapine, iloperidone, olanzapine, paliperidone, quetiapine, risperidone, or ziprasidone.

Embodiment 24. The pharmaceutical preparation of any one of Embodiments 18-23, wherein the antipsychotic drug is formulated in a first pharmaceutical composition and the VMAT2 inhibitor is formulated in a second pharmaceutical composition.

Embodiment 25. The pharmaceutical preparation of any one of Embodiments 18-24, wherein the therapeutically effective amount of the antipsychotic drug is 10 to 90% less than the therapeutically effective amount of the antipsychotic drug when administered in the absence of the VMAT2 inhibitor.

Embodiment 26. The pharmaceutical preparation of any one of Embodiments 18-24, wherein the therapeutically effective amount of the antipsychotic drug is at least 25% less than the therapeutically effective amount of the antipsychotic drug when administered in the absence of the VMAT2 inhibitor.

Embodiment 27. The pharmaceutical preparation of any one of Embodiments 18-24, wherein the therapeutically effective amount of the antipsychotic drug is at least 50% less than the therapeutically effective amount of the antipsychotic drug when administered in the absence of the VMAT2 inhibitor.

Embodiment 28. The pharmaceutical preparation of any one of Embodiments 18-27 wherein the VMAT2 inhibitor is tetrabenazine (3-isobutyl-9, 10-dimethoxy-1,3,4,6,7,11b-hexahydro-2H-pyrido[2,1-a]isoquinolin-2-one).

Embodiment 29. The pharmaceutical preparation of any one of Embodiments 18-27 wherein the VMAT2 inhibitor is (2R,3R,11bR)-3-isobutyl-9,10-dimethoxy-1,3,4,6,7,11b-hexahydro-2H-pyrido[2,1-a]isoquinolin-2-ol(R,R,R DHTBZ), or a precursor thereof.

Embodiment 30. The pharmaceutical preparation of any one of Embodiments 18-27, wherein the VMAT2 inhibitor is (S)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester.

Embodiment 31. The pharmaceutical preparation of any one of Embodiments 18-27, wherein the VMAT2 inhibitor is [(2R,3S,11bR)-9,10-Dimethoxy-3-(2-methylpropyl)-1H, 2H,3H,4H,6H,7H,11bH-pyrido[2,1-a]isoquinolin-2-yl]methanol, or a precursor thereof.

Embodiment 32. The pharmaceutical preparation of any one of Embodiments 18-27, wherein the VMAT2 inhibitor is 3-isobutyl-9,10-$d_6$-dimethoxy-1,3,4,6,7,11b-hexahydro-2H-pyrido[2,1-a]isoquinolin-2-one ($d_6$-TBZ).

Embodiment 33. A method for enhancing efficacy of an antipsychotic drug comprising administering to a subject a combination of (a) the antipsychotic drug, and (b) a VMAT2 inhibitor.

Embodiment 34. The method of Embodiment 33, wherein enhancing efficacy of the antipsychotic drug comprises decreasing the amount of the antipsychotic that is therapeutically effective.

Embodiment 35. The method of Embodiment 33, wherein the amount of the antipsychotic drug that is therapeutically effective is 10 to 90% less than the amount of the antipsychotic drug that is therapeutically effective when the antipsychotic drug is administered in the absence of the VMAT2 inhibitor.

Embodiment 36. The method of Embodiment 33, wherein the amount of the antipsychotic drug that is therapeutically effective is at least 25% less than the amount of the antipsychotic drug that is therapeutically effective when the antipsychotic drug is administered in the absence of the VMAT2 inhibitor.

Embodiment 37. The method of Embodiments 33, wherein the amount of the antipsychotic drug that is therapeutically effective is at least 50% less than the amount of the antipsychotic drug that is therapeutically effective when the antipsychotic drug is administered in the absence of the VMAT2 inhibitor.

Embodiment 38. The method of any one of Embodiments 33-37, wherein the antipsychotic drug is a typical antipsychotic drug.

Embodiment 39. The method of Embodiment 38, wherein the typical antipsychotic drug is fluphenazine, haloperidol, loxapine, molindone, perphenazine, pimozide, sulpiride, thioridazine, or trifluoperazine.

Embodiment 40. The method of any one of Embodiments 33-37, wherein the antipsychotic drug is an atypical antipsychotic drug.

Embodiment 41. The method of Embodiment 40, wherein the atypical antipsychotic drug is aripiprazole, asenapine, clozapine, iloperidone, olanzapine, paliperidone, quetiapine, risperidone, or ziprasidone.

Embodiment 42. The method of any one of Embodiments 33-41, wherein the VMAT2 inhibitor is tetrabenazine (3-isobutyl-9,10-dimethoxy-1,3,4,6,7,11b-hexahydro-2H-pyrido[2,1-a]isoquinolin-2-one).

Embodiment 43. The method of any one of Embodiments 33-41, wherein the VMAT2 inhibitor is (2R,3R,11bR)-3-isobutyl-9,10-dimethoxy-1,3,4,6,7,11b-hexahydro-2H-pyrido[2,1-a]isoquinolin-2-ol (R,R,R DHTBZ), or a precursor thereof.

Embodiment 44. The method of any one of Embodiments 33-41, wherein the VMAT2 inhibitor is (S)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester.

Embodiment 45. The method of any one of Embodiments 33-41, wherein the VMAT2 inhibitor is [(2R,3S,11bR)-9,10-Dimethoxy-3-(2-methylpropyl)-1H,2H,3H,4H,6H,7H,11bH-pyrido[2,1-a]isoquinolin-2-yl]methanol, or a precursor thereof.

Embodiment 46. The method of any one of Embodiments 33-41, wherein the VMAT2 inhibitor is 3-isobutyl-9,10-$d_6$-dimethoxy-1,3,4,6,7,11b-hexahydro-2H-pyrido[2,1-a]isoquinolin-2-one ($d_6$-TBZ).

Embodiment 47. A pharmaceutical preparation comprising an antipsychotic drug and a VMAT2 inhibitor, wherein the preparation is effective for treating a neuropsychiatric disorder, and wherein the amount of the antipsychotic drug is subtherapeutic compared with the therapeutic amount of the antipsychotic drug when used alone for treating the neuropsychiatric disorder in the absence of the VMAT2 inhibitor.

Embodiment 48. A pharmaceutical preparation comprising synergistically effective amounts of an antipsychotic drug and a VMAT2 inhibitor.

Embodiment 49. The pharmaceutical preparation of Embodiment 47 or Embodiment 48 wherein the antipsychotic drug is a typical antipsychotic drug.

Embodiment 50. The pharmaceutical composition of Embodiment 49 wherein the typical antipsychotic drug is fluphenazine, haloperidol, loxapine, molindone, perphenazine, pimozide, sulpiride, thioridazine, or trifluoperazine.

Embodiment 51. The pharmaceutical preparation of Embodiment 47 or Embodiment 48 wherein the antipsychotic drug is an atypical antipsychotic drug.

Embodiment 52. The pharmaceutical composition of Embodiment 51 wherein the atypical antipsychotic drug is aripiprazole, asenapine, clozapine, iloperidone, olanzapine, paliperidone, quetiapine, risperidone, or ziprasidone.

Embodiment 53. The pharmaceutical preparation of any one of Embodiments 47-52 wherein the VMAT2 inhibitor is tetrabenazine (3-isobutyl-9,10-dimethoxy-1,3,4,6,7,11b-hexahydro-2H-pyrido[2,1-a]isoquinolin-2-one).

Embodiment 54. The pharmaceutical preparation of any one of Embodiments 47-52 wherein the VMAT2 inhibitor is (2R,3R,11bR)-3-isobutyl-9,10-dimethoxy-1,3,4,6,7,11b-hexahydro-2H-pyrido[2,1-a]isoquinolin-2-ol(R,R,R DHTBZ), or a precursor thereof.

Embodiment 55. The pharmaceutical preparation of any one of Embodiments 47-52, wherein the VMAT2 inhibitor is (S)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester.

Embodiment 56. The pharmaceutical preparation of any one of Embodiments 47-52, wherein the VMAT2 inhibitor is [(2R,3S,11bR)-9,10-Dimethoxy-3-(2-methylpropyl)-1H, 2H,3H,4H,6H,7H,11bH-pyrido[2,1-a]isoquinolin-2-yl]methanol, or a precursor thereof.

Embodiment 57. The pharmaceutical preparation of any one of Embodiments 47-52, wherein the VMAT2 inhibitor is 3-isobutyl-9,10-$d_6$-dimethoxy-1,3,4,6,7,11b-hexahydro-2H-pyrido[2,1-a]isoquinolin-2-one ($d_6$-TBZ).

Embodiment 58. The pharmaceutical preparation of any one of Embodiments 47-57 wherein the antipsychotic drug and the VMAT2 inhibitor are formulated in the same pharmaceutical composition with at least one pharmaceutically acceptable excipient.

Embodiment 59. The pharmaceutical preparation of any one of Embodiments 47-58 wherein the antipsychotic drug is formulated in a first pharmaceutical composition with at least one pharmaceutically acceptable excipient and the VMAT2 inhibitor is formulated in a second pharmaceutical composition with at least one pharmaceutically acceptable excipient.

Embodiment 60. The pharmaceutical composition of any one of Embodiments 47-59 wherein the neuropsychiatric disorder is schizophrenia, schizoaffective disorder, bipolar disorder, major depressive disorder (MDD), or autism.

All U.S. patents, U.S. patent application publications, U.S. patent applications, foreign patents, foreign patent applications and non-patent publications referred to in this specification and/or listed in the Application Data Sheet are incorporated herein by reference, in their entirety. U.S. Patent Application No. 61/937,223, filed Feb. 7, 2014, is incorporated herein in its entirety. Aspects of the embodiments can be modified, if necessary to employ concepts of the various patents, applications and publications to provide yet further embodiments.

These and other changes can be made to the embodiments in light of the above-detailed description. Although specific embodiments have been described herein for purposes of illustration, various modifications may be made without departing from the spirit and scope of the invention. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

I claim the following:

1. A method for treating a neuropsychiatric disorder in a subject comprising administering to the subject (a) an antipsychotic drug and (b) a VMAT2 inhibitor, wherein the therapeutically effective amount of the antipsychotic drug administered to the subject is less than the therapeutically effective amount of the antipsychotic drug when administered in the absence of the VMAT2 inhibitor wherein the neuropsychiatric disorder is schizophrenia, schizoaffective disorder, bipolar disorder, major depressive disorder (MDD) or autism and wherein the antipsychotic drug is aripiprazole, asenapine, clozapine, iloperidone, olanzapine, paliperidone, questiapine, risperidone, or ziprasidone and wherein the VMAT2 inhibitor is tetrabenazine (3-isobutyl-9,10-dimethoxy-1,3,4,6,7,11b-hexahydro-2H-pyrido[2,1-a]isoquinolin-2-one), (2R,3R, 11bR)-3-isobutyl-9,10-dimethoxy-1,3,4,6,7,11b-hexahydro-2H-pyrido[2,1-a]isoquinolin-2-ol (R,R,R DHTBZ), (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2yl ester, [(2R,3S,11bR)-9,10-dimethoxy-3-(2-methylpropyl)-1H,2H,3H,4H,6H,7H,11bH-pyrido[2,1-a]isoquinolin-2yl]methanol or 3-isobutyl-9,10-d6-dimethoxy-1,3,4,6,7,11b-hexahydro-2H-pyrido[2,1-a]isoquinolin-2-one (d6-TBZ).

2. The method of claim 1, wherein the antipsychotic drug and the VMAT2 inhibitor are administered concurrently.

3. The method of claim 2, wherein the antipsychotic drug and the VMAT2 inhibitor are formulated in the same pharmaceutical composition.

4. The method of claim 1, wherein the antipsychotic drug is formulated in a first pharmaceutical composition and the VMAT2 inhibitor is formulated in a second pharmaceutical composition.

5. The method of claim 1, wherein the therapeutically effective amount of the antipsychotic drug is 10 to 90% less than the therapeutically effective amount of the antipsychotic drug when administered in the absence of the VMAT2 inhibitor.

6. The method of claim 1, wherein the therapeutically effective amount of the antipsychotic drug is at least 25% less than the therapeutically effective amount of the antipsychotic drug when administered in the absence of the VMAT2 inhibitor.

7. The method of claim 1, wherein the therapeutically effective amount of the antipsychotic drug is at least 50% less than the therapeutically effective amount of the antipsychotic drug when administered in the absence of the VMAT2 inhibitor.

8. The method of any one of claims 1, 2-4, or 5-7 wherein the VMAT2 inhibitor is tetrabenazine (3-isobutyl-9,10-dimethoxy-1,3,4,6,7,11b-hexahydro-2H-pyrido[2,1-a]isoquinolin-2-one).

9. The method of any one of claims 1, 2-4, or 5-7 wherein the VMAT2 inhibitor is (2R,3R,11bR)-3-isobutyl-9,10-dimethoxy-1,3,4,6,7,11b-hexahydro-2H-pyrido[2,1-a]isoquinolin-2-ol (R,R,R DHTBZ).

10. The method of any one of claims 1, 2-4 or 5-7 wherein the VMAT2 inhibitor is (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester.

11. The method of any one of claims 1, 2-4, or 5-7 wherein the VMAT2 inhibitor is [(2R,3S,11bR)-9,10-dimethoxy-3-(2-methylpropyl)-1H,2H,3H,4H,6H,7H,11bH-pyrido[2,1-a]isoquinolin-2-yl]methanol.

12. The method of any one of claims 1-7, wherein the VMAT2 inhibitor is 3-isobutyl-9,10-$d_6$-dimethoxy-1,3,4,6,7,11b-hexahydro-2H-pyrido[2,1-a]isoquinolin-2-one ($d_6$-TBZ).

* * * * *

UNITED STATES PATENT AND TRADEMARK OFFICE
CERTIFICATE OF CORRECTION

PATENT NO. : 9,782,398 B2
APPLICATION NO. : 15/116786
DATED : October 10, 2017
INVENTOR(S) : Hoare et al.

It is certified that error appears in the above-identified patent and that said Letters Patent is hereby corrected as shown below:

On the Title Page

Item (12) update to the following:
Hoare et al.

Please add the following Inventors to item (72), should read as follows:
Samuel Roger Jesse Hoare, San Diego, CA (US)
Neil. J. Ashweek, Escondido, CA, (US)
Dimitri E. Grigoriadis, San Diego, CA, (US)

Signed and Sealed this
Twenty-third Day of May, 2023

Katherine Kelly Vidal
*Director of the United States Patent and Trademark Office*